United States Patent
Maile et al.

(10) Patent No.: US 10,583,303 B2
(45) Date of Patent: Mar. 10, 2020

(54) DEVICES AND METHODS FOR WIRELESSLY RECHARGING A RECHARGEABLE BATTERY OF AN IMPLANTABLE MEDICAL DEVICE

(71) Applicants: CARDIAC PACEMAKERS, INC., St. Paul, MN (US); NDSU RESEARCH FOUNDATION, Fargo, ND (US)

(72) Inventors: Keith R. Maile, New Brighton, MN (US); Benjamin Braaten, Fargo, ND (US); Daniel Ewert, Fargo, ND (US)

(*) Notice: Subject to any disclaimer, the term of this patent is extended or adjusted under 35 U.S.C. 154(b) by 186 days.

(21) Appl. No.: 15/410,348

(22) Filed: Jan. 19, 2017

(65) Prior Publication Data

US 2017/0203109 A1 Jul. 20, 2017

Related U.S. Application Data

(60) Provisional application No. 62/280,644, filed on Jan. 19, 2016.

(51) Int. Cl.
| | | |
|---|---|---|
| *A61N 1/37* | (2006.01) | |
| *A61N 1/378* | (2006.01) | |
| *A61N 1/362* | (2006.01) | |
| *A61N 1/372* | (2006.01) | |

(Continued)

(52) U.S. Cl.
CPC .......... *A61N 1/3787* (2013.01); *A61N 1/362* (2013.01); *A61N 1/3756* (2013.01); *A61N 1/37223* (2013.01); *A61N 1/36* (2013.01); *A61N 1/37229* (2013.01)

(58) Field of Classification Search
USPC ..................................................... 607/33, 59
See application file for complete search history.

(56) References Cited

U.S. PATENT DOCUMENTS

| | | |
|---|---|---|
| 3,835,864 A | 9/1974 | Rasor et al. |
| 3,943,936 A | 3/1976 | Rasor et al. |
| 4,142,530 A | 3/1979 | Wittkampf |

(Continued)

FOREIGN PATENT DOCUMENTS

| | | |
|---|---|---|
| AU | 2008279789 B2 | 10/2011 |
| AU | 2008329620 B2 | 5/2014 |

(Continued)

OTHER PUBLICATIONS

US 8,886,318 B2, 11/2014, Jacobson et al. (withdrawn)

(Continued)

*Primary Examiner* — Nicole F Lavert
(74) *Attorney, Agent, or Firm* — Seager, Tufte & Wickhem LLP

(57) ABSTRACT

Implantable medical devices such as leadless cardiac pacemakers may include a rechargeable battery, and a receiving antenna for receiving radiative energy from an external transmitter. Energy captured by the receiving antenna of the implantable medical device may be converted into electrical energy that may be used to recharge the rechargeable battery of the implantable medical device. Since the rechargeable battery does not have to initially store sufficient energy to power the implantable medical device over its entire useful life, the battery itself and thus the implanted medical device can be made smaller while still achieving device longevity expectations.

20 Claims, 14 Drawing Sheets

(51) Int. Cl.
*A61N 1/375* (2006.01)
*A61N 1/36* (2006.01)

(56) References Cited

U.S. PATENT DOCUMENTS

| | | |
|---|---|---|
| 4,151,513 A | 4/1979 | Menken et al. |
| 4,157,720 A | 6/1979 | Greatbatch |
| RE30,366 E | 8/1980 | Rasor et al. |
| 4,243,045 A | 1/1981 | Maas |
| 4,250,884 A | 2/1981 | Hartlaub et al. |
| 4,256,115 A | 3/1981 | Bilitch |
| 4,263,919 A | 4/1981 | Levin |
| 4,310,000 A | 1/1982 | Lindemans |
| 4,312,354 A | 1/1982 | Walters |
| 4,323,081 A | 4/1982 | Wiebusch |
| 4,357,946 A | 11/1982 | Dutcher et al. |
| 4,365,639 A | 12/1982 | Goldreyer |
| 4,440,173 A | 4/1984 | Hudziak et al. |
| 4,476,868 A | 10/1984 | Thompson |
| 4,522,208 A | 6/1985 | Buffet |
| 4,537,200 A | 8/1985 | Widrow |
| 4,556,063 A | 12/1985 | Thompson et al. |
| 4,562,841 A | 1/1986 | Brockway et al. |
| 4,593,702 A | 6/1986 | Kepski et al. |
| 4,593,955 A | 6/1986 | Leiber |
| 4,630,611 A | 12/1986 | King |
| 4,635,639 A | 1/1987 | Hakala et al. |
| 4,674,508 A | 6/1987 | DeCote |
| 4,712,554 A | 12/1987 | Garson |
| 4,729,376 A | 3/1988 | DeCote |
| 4,754,753 A | 7/1988 | King |
| 4,759,366 A | 7/1988 | Callaghan |
| 4,776,338 A | 10/1988 | Lekholm et al. |
| 4,787,389 A | 11/1988 | Tarjan |
| 4,793,353 A | 12/1988 | Borkan |
| 4,819,662 A | 4/1989 | Heil et al. |
| 4,858,610 A | 8/1989 | Callaghan et al. |
| 4,886,064 A | 12/1989 | Strandberg |
| 4,887,609 A | 12/1989 | Cole, Jr. |
| 4,928,688 A | 5/1990 | Mower |
| 4,967,746 A | 11/1990 | Vandegriff |
| 4,987,897 A | 1/1991 | Funke |
| 4,989,602 A | 2/1991 | Sholder et al. |
| 5,012,806 A | 5/1991 | De Bellis |
| 5,036,849 A | 8/1991 | Hauck et al. |
| 5,040,534 A | 8/1991 | Mann et al. |
| 5,058,581 A | 10/1991 | Silvian |
| 5,078,134 A | 1/1992 | Heilman et al. |
| 5,109,845 A | 5/1992 | Yuuchi et al. |
| 5,113,859 A | 5/1992 | Funke |
| 5,117,824 A | 6/1992 | Keimel et al. |
| 5,127,401 A | 7/1992 | Grevious et al. |
| 5,133,353 A | 7/1992 | Hauser |
| 5,144,950 A | 9/1992 | Stoop et al. |
| 5,170,784 A | 12/1992 | Ramon et al. |
| 5,179,945 A | 1/1993 | Van Hofwegen et al. |
| 5,193,539 A | 3/1993 | Schulman et al. |
| 5,193,540 A | 3/1993 | Schulman et al. |
| 5,241,961 A | 9/1993 | Henry |
| 5,243,977 A | 9/1993 | Trabucco et al. |
| 5,254,997 A | 10/1993 | Cohn |
| 5,259,387 A | 11/1993 | dePinto |
| 5,269,326 A | 12/1993 | Verrier |
| 5,284,136 A | 2/1994 | Hauck et al. |
| 5,300,107 A | 4/1994 | Stokes et al. |
| 5,301,677 A | 4/1994 | Hsung |
| 5,305,760 A | 4/1994 | McKown et al. |
| 5,312,439 A | 5/1994 | Loeb |
| 5,313,953 A | 5/1994 | Yomtov et al. |
| 5,314,459 A | 5/1994 | Swanson et al. |
| 5,318,597 A | 6/1994 | Hauck et al. |
| 5,324,316 A | 6/1994 | Schulman et al. |
| 5,331,966 A | 7/1994 | Bennett et al. |
| 5,334,222 A | 8/1994 | Salo et al. |
| 5,342,408 A | 8/1994 | Decoriolis et al. |
| 5,370,667 A | 12/1994 | Alt |
| 5,372,606 A | 12/1994 | Lang et al. |
| 5,376,106 A | 12/1994 | Stahmann et al. |
| 5,383,915 A | 1/1995 | Adams |
| 5,388,578 A | 2/1995 | Yomtov et al. |
| 5,404,877 A | 4/1995 | Nolan et al. |
| 5,405,367 A | 4/1995 | Schulman et al. |
| 5,411,031 A | 5/1995 | Yomtov |
| 5,411,525 A | 5/1995 | Swanson et al. |
| 5,411,535 A | 5/1995 | Fujii et al. |
| 5,456,691 A | 10/1995 | Snell |
| 5,458,622 A | 10/1995 | Alt |
| 5,466,246 A | 11/1995 | Silvian |
| 5,468,254 A | 11/1995 | Hahn et al. |
| 5,472,453 A | 12/1995 | Alt |
| 5,522,866 A | 6/1996 | Fernald |
| 5,540,727 A | 7/1996 | Tockman et al. |
| 5,545,186 A | 8/1996 | Olson et al. |
| 5,545,202 A | 8/1996 | Dahl et al. |
| 5,571,146 A | 11/1996 | Jones et al. |
| 5,591,214 A | 1/1997 | Lu |
| 5,620,466 A | 4/1997 | Haefner et al. |
| 5,634,938 A | 6/1997 | Swanson et al. |
| 5,649,968 A | 7/1997 | Alt et al. |
| 5,662,688 A | 9/1997 | Haefner et al. |
| 5,674,259 A | 10/1997 | Gray |
| 5,683,426 A | 11/1997 | Greenhut et al. |
| 5,683,432 A | 11/1997 | Goedeke et al. |
| 5,706,823 A | 1/1998 | Wodlinger |
| 5,709,215 A | 1/1998 | Perttu et al. |
| 5,720,770 A | 2/1998 | Nappholz et al. |
| 5,728,154 A | 3/1998 | Crossett et al. |
| 5,741,314 A | 4/1998 | Daly et al. |
| 5,741,315 A | 4/1998 | Lee et al. |
| 5,752,976 A | 5/1998 | Duffin et al. |
| 5,752,977 A | 5/1998 | Grevious et al. |
| 5,755,736 A | 5/1998 | Gillberg et al. |
| 5,759,199 A | 6/1998 | Snell et al. |
| 5,774,501 A | 6/1998 | Halpern et al. |
| 5,792,195 A | 8/1998 | Carlson et al. |
| 5,792,202 A | 8/1998 | Rueter |
| 5,792,203 A | 8/1998 | Schroeppel |
| 5,792,205 A | 8/1998 | Alt et al. |
| 5,792,208 A | 8/1998 | Gray |
| 5,814,089 A | 9/1998 | Stokes et al. |
| 5,827,216 A | 10/1998 | Igo et al. |
| 5,836,985 A | 11/1998 | Goyal et al. |
| 5,836,987 A | 11/1998 | Baumann et al. |
| 5,842,977 A | 12/1998 | Lesho et al. |
| 5,855,593 A | 1/1999 | Olson et al. |
| 5,873,894 A | 2/1999 | Vandegriff et al. |
| 5,891,184 A | 4/1999 | Lee et al. |
| 5,897,586 A | 4/1999 | Molina |
| 5,899,876 A | 5/1999 | Flower |
| 5,899,928 A | 5/1999 | Sholder et al. |
| 5,919,214 A | 7/1999 | Ciciarelli et al. |
| 5,935,078 A | 8/1999 | Feierbach |
| 5,941,906 A | 8/1999 | Barreras et al. |
| 5,944,744 A | 8/1999 | Paul et al. |
| 5,954,757 A | 9/1999 | Gray |
| 5,978,713 A | 11/1999 | Prutchi et al. |
| 5,991,660 A | 11/1999 | Goyal |
| 5,991,661 A | 11/1999 | Park et al. |
| 5,999,848 A | 12/1999 | Gord et al. |
| 5,999,857 A | 12/1999 | Weijand et al. |
| 6,016,445 A | 1/2000 | Baura |
| 6,026,320 A | 2/2000 | Carlson et al. |
| 6,029,085 A | 2/2000 | Olson et al. |
| 6,041,250 A | 3/2000 | dePinto |
| 6,044,298 A | 3/2000 | Salo et al. |
| 6,044,300 A | 3/2000 | Gray |
| 6,055,454 A | 4/2000 | Heemels |
| 6,073,050 A | 6/2000 | Griffith |
| 6,076,016 A | 6/2000 | Feierbach |
| 6,077,236 A | 6/2000 | Cunningham |
| 6,080,187 A | 6/2000 | Alt et al. |
| 6,083,248 A | 7/2000 | Thompson |
| 6,106,551 A | 8/2000 | Crossett et al. |
| 6,115,636 A | 9/2000 | Ryan |

(56) References Cited

U.S. PATENT DOCUMENTS

| | | |
|---|---|---|
| 6,128,526 A | 10/2000 | Stadler et al. |
| 6,141,581 A | 10/2000 | Olson et al. |
| 6,141,588 A | 10/2000 | Cox et al. |
| 6,141,592 A | 10/2000 | Pauly |
| 6,144,879 A | 11/2000 | Gray |
| 6,162,195 A | 12/2000 | Igo et al. |
| 6,164,284 A | 12/2000 | Schulman et al. |
| 6,167,310 A | 12/2000 | Grevious |
| 6,201,993 B1 | 3/2001 | Kruse et al. |
| 6,208,894 B1 | 3/2001 | Schulman et al. |
| 6,211,799 B1 | 4/2001 | Post et al. |
| 6,221,011 B1 | 4/2001 | Bardy |
| 6,240,316 B1 | 5/2001 | Richmond et al. |
| 6,240,317 B1 | 5/2001 | Villaseca et al. |
| 6,256,534 B1 | 7/2001 | Dahl |
| 6,259,947 B1 | 7/2001 | Olson et al. |
| 6,266,558 B1 | 7/2001 | Gozani et al. |
| 6,266,567 B1 | 7/2001 | Ishikawa et al. |
| 6,270,457 B1 | 8/2001 | Bardy |
| 6,272,377 B1 | 8/2001 | Sweeney et al. |
| 6,273,856 B1 | 8/2001 | Sun et al. |
| 6,277,072 B1 | 8/2001 | Bardy |
| 6,280,380 B1 | 8/2001 | Bardy |
| 6,285,907 B1 | 9/2001 | Kramer et al. |
| 6,292,698 B1 | 9/2001 | Duffin et al. |
| 6,295,473 B1 | 9/2001 | Rosar |
| 6,297,943 B1 | 10/2001 | Carson |
| 6,298,271 B1 | 10/2001 | Weijand |
| 6,307,751 B1 | 10/2001 | Bodony et al. |
| 6,312,378 B1 | 11/2001 | Bardy |
| 6,315,721 B2 | 11/2001 | Schulman et al. |
| 6,336,903 B1 | 1/2002 | Bardy |
| 6,345,202 B2 | 2/2002 | Richmond et al. |
| 6,351,667 B1 | 2/2002 | Godie |
| 6,351,669 B1 | 2/2002 | Hartley et al. |
| 6,353,759 B1 | 3/2002 | Hartley et al. |
| 6,358,203 B2 | 3/2002 | Bardy |
| 6,361,780 B1 | 3/2002 | Ley et al. |
| 6,368,284 B1 | 4/2002 | Bardy |
| 6,371,922 B1 | 4/2002 | Baumann et al. |
| 6,398,728 B1 | 6/2002 | Bardy |
| 6,400,982 B2 | 6/2002 | Sweeney et al. |
| 6,400,990 B1 | 6/2002 | Silvian |
| 6,408,208 B1 | 6/2002 | Sun |
| 6,409,674 B1 | 6/2002 | Brockway et al. |
| 6,411,848 B2 | 6/2002 | Kramer et al. |
| 6,424,865 B1 | 7/2002 | Ding |
| 6,434,429 B1 | 8/2002 | Kraus et al. |
| 6,438,410 B2 | 8/2002 | Hsu et al. |
| 6,438,417 B1 | 8/2002 | Rockwell et al. |
| 6,438,421 B1 | 8/2002 | Stahmann et al. |
| 6,440,066 B1 | 8/2002 | Bardy |
| 6,441,747 B1 | 8/2002 | Khair et al. |
| 6,442,426 B1 | 8/2002 | Kroll |
| 6,442,432 B2 | 8/2002 | Lee |
| 6,443,891 B1 | 9/2002 | Grevious |
| 6,445,953 B1 | 9/2002 | Bulkes et al. |
| 6,453,200 B1 | 9/2002 | Koslar |
| 6,459,929 B1 | 10/2002 | Hopper et al. |
| 6,470,215 B1 | 10/2002 | Kraus et al. |
| 6,471,645 B1 | 10/2002 | Warkentin et al. |
| 6,480,745 B2 | 11/2002 | Nelson et al. |
| 6,487,443 B2 | 11/2002 | Olson et al. |
| 6,490,487 B1 | 12/2002 | Kraus et al. |
| 6,498,951 B1 | 12/2002 | Larson et al. |
| 6,507,755 B1 | 1/2003 | Gozani et al. |
| 6,507,759 B1 | 1/2003 | Prutchi et al. |
| 6,512,940 B1 | 1/2003 | Brabec et al. |
| 6,522,915 B1 | 2/2003 | Ceballos et al. |
| 6,526,311 B2 | 2/2003 | Begemann |
| 6,539,253 B2 | 3/2003 | Thompson et al. |
| 6,542,775 B2 | 4/2003 | Ding et al. |
| 6,553,258 B2 | 4/2003 | Stahmann et al. |
| 6,561,975 B1 | 5/2003 | Pool et al. |
| 6,564,807 B1 | 5/2003 | Schulman et al. |
| 6,574,506 B2 | 6/2003 | Kramer et al. |
| 6,584,351 B1 | 6/2003 | Ekwall |
| 6,584,352 B2 | 6/2003 | Combs et al. |
| 6,597,948 B1 | 7/2003 | Rockwell et al. |
| 6,597,951 B2 | 7/2003 | Kramer et al. |
| 6,622,046 B2 | 9/2003 | Fraley et al. |
| 6,628,985 B2 | 9/2003 | Sweeney et al. |
| 6,647,292 B1 | 11/2003 | Bardy et al. |
| 6,666,844 B1 | 12/2003 | Igo et al. |
| 6,689,117 B2 | 2/2004 | Sweeney et al. |
| 6,690,959 B2 | 2/2004 | Thompson |
| 6,694,189 B2 | 2/2004 | Begemann |
| 6,704,602 B2 | 3/2004 | Berg et al. |
| 6,718,212 B2 | 4/2004 | Parry et al. |
| 6,721,597 B1 | 4/2004 | Bardy et al. |
| 6,738,670 B1 | 5/2004 | Almendinger et al. |
| 6,746,797 B2 | 6/2004 | Benson et al. |
| 6,749,566 B2 | 6/2004 | Russ |
| 6,758,810 B2 | 7/2004 | Lebel et al. |
| 6,763,269 B2 | 7/2004 | Cox |
| 6,778,860 B2 | 8/2004 | Ostroff et al. |
| 6,788,971 B1 | 9/2004 | Sloman et al. |
| 6,788,974 B2 | 9/2004 | Bardy et al. |
| 6,804,558 B2 | 10/2004 | Haller et al. |
| 6,807,442 B1 | 10/2004 | Myklebust et al. |
| 6,847,844 B2 | 1/2005 | Sun et al. |
| 6,871,095 B2 | 3/2005 | Stahmann et al. |
| 6,878,112 B2 | 4/2005 | Linberg et al. |
| 6,885,889 B2 | 4/2005 | Chinchoy |
| 6,892,094 B2 | 5/2005 | Ousdigian et al. |
| 6,897,788 B2 | 5/2005 | Khair et al. |
| 6,904,315 B2 | 6/2005 | Panken et al. |
| 6,922,592 B2 | 7/2005 | Thompson et al. |
| 6,931,282 B2 | 8/2005 | Esler |
| 6,934,585 B1 | 8/2005 | Schloss et al. |
| 6,957,107 B2 | 10/2005 | Rogers et al. |
| 6,978,176 B2 | 12/2005 | Lattouf |
| 6,985,773 B2 | 1/2006 | Von Arx et al. |
| 6,990,375 B2 | 1/2006 | Kloss et al. |
| 7,001,366 B2 | 2/2006 | Ballard |
| 7,003,350 B2 | 2/2006 | Denker et al. |
| 7,006,864 B2 | 2/2006 | Echt et al. |
| 7,013,178 B2 | 3/2006 | Reinke et al. |
| 7,027,871 B2 | 4/2006 | Burnes et al. |
| 7,050,849 B2 | 5/2006 | Echt et al. |
| 7,060,031 B2 | 6/2006 | Webb et al. |
| 7,063,693 B2 | 6/2006 | Guenst |
| 7,082,336 B2 | 7/2006 | Ransbury et al. |
| 7,085,606 B2 | 8/2006 | Flach et al. |
| 7,092,758 B2 | 8/2006 | Sun et al. |
| 7,110,824 B2 | 9/2006 | Amundson et al. |
| 7,120,504 B2 | 10/2006 | Osypka |
| 7,130,681 B2 | 10/2006 | Gebhardt et al. |
| 7,139,613 B2 | 11/2006 | Reinke et al. |
| 7,142,912 B2 | 11/2006 | Wagner et al. |
| 7,146,225 B2 | 12/2006 | Guenst et al. |
| 7,146,226 B2 | 12/2006 | Lau et al. |
| 7,149,581 B2 | 12/2006 | Goedeke |
| 7,149,588 B2 | 12/2006 | Lau et al. |
| 7,158,839 B2 | 1/2007 | Lau |
| 7,162,307 B2 | 1/2007 | Patrias |
| 7,164,952 B2 | 1/2007 | Lau et al. |
| 7,177,700 B1 | 2/2007 | Cox |
| 7,181,505 B2 | 2/2007 | Haller et al. |
| 7,184,830 B2 | 2/2007 | Echt et al. |
| 7,186,214 B2 | 3/2007 | Ness |
| 7,191,015 B2 | 3/2007 | Lamson et al. |
| 7,200,437 B1 | 4/2007 | Nabutovsky et al. |
| 7,200,439 B2 | 4/2007 | Zdeblick et al. |
| 7,206,423 B1 | 4/2007 | Feng et al. |
| 7,209,785 B2 | 4/2007 | Kim et al. |
| 7,209,790 B2 | 4/2007 | Thompson et al. |
| 7,211,884 B1 | 5/2007 | Davis et al. |
| 7,212,871 B1 | 5/2007 | Morgan |
| 7,226,440 B2 | 6/2007 | Gelfand et al. |
| 7,228,183 B2 | 6/2007 | Sun et al. |
| 7,236,821 B2 | 6/2007 | Cates et al. |
| 7,236,829 B1 | 6/2007 | Farazi et al. |
| 7,254,448 B2 | 8/2007 | Almendinger et al. |

(56) References Cited

U.S. PATENT DOCUMENTS

| | | |
|---|---|---|
| 7,260,436 B2 | 8/2007 | Kilgore et al. |
| 7,270,669 B1 | 9/2007 | Sra |
| 7,272,448 B1 | 9/2007 | Morgan et al. |
| 7,277,755 B1 | 10/2007 | Falkenberg et al. |
| 7,280,872 B1 | 10/2007 | Mosesov et al. |
| 7,288,096 B2 | 10/2007 | Chin |
| 7,289,847 B1 | 10/2007 | Gill et al. |
| 7,289,852 B2 | 10/2007 | Helfinstine et al. |
| 7,289,853 B1 | 10/2007 | Campbell et al. |
| 7,289,855 B2 | 10/2007 | Nghiem et al. |
| 7,302,294 B2 | 11/2007 | Kamath et al. |
| 7,305,266 B1 | 12/2007 | Kroll |
| 7,310,556 B2 | 12/2007 | Bulkes |
| 7,319,905 B1 | 1/2008 | Morgan et al. |
| 7,333,853 B2 | 2/2008 | Mazar et al. |
| 7,336,994 B2 | 2/2008 | Hettrick et al. |
| 7,347,819 B2 | 3/2008 | Lebel et al. |
| 7,366,572 B2 | 4/2008 | Heruth et al. |
| 7,373,207 B2 | 5/2008 | Lattouf |
| 7,384,403 B2 | 6/2008 | Sherman |
| 7,386,342 B1 | 6/2008 | Falkenberg et al. |
| 7,392,090 B2 | 6/2008 | Sweeney et al. |
| 7,406,105 B2 | 7/2008 | DelMain et al. |
| 7,406,349 B2 | 7/2008 | Seeberger et al. |
| 7,410,497 B2 | 8/2008 | Hastings et al. |
| 7,425,200 B2 | 9/2008 | Brockway et al. |
| 7,433,739 B1 | 10/2008 | Salys et al. |
| 7,496,409 B2 | 2/2009 | Greenhut et al. |
| 7,496,410 B2 | 2/2009 | Heil |
| 7,502,652 B2 | 3/2009 | Gaunt et al. |
| 7,512,448 B2 | 3/2009 | Malick et al. |
| 7,515,969 B2 | 4/2009 | Tockman et al. |
| 7,526,342 B2 | 4/2009 | Chin et al. |
| 7,529,589 B2 | 5/2009 | Williams et al. |
| 7,532,933 B2 | 5/2009 | Hastings et al. |
| 7,536,222 B2 | 5/2009 | Bardy et al. |
| 7,536,224 B2 | 5/2009 | Ritscher et al. |
| 7,539,541 B2 | 5/2009 | Quiles et al. |
| 7,544,197 B2 | 6/2009 | Kelsch et al. |
| 7,558,631 B2 | 7/2009 | Cowan et al. |
| 7,565,195 B1 | 7/2009 | Kroll et al. |
| 7,584,002 B2 | 9/2009 | Burnes et al. |
| 7,590,455 B2 | 9/2009 | Heruth et al. |
| 7,606,621 B2 | 10/2009 | Brisken et al. |
| 7,610,088 B2 | 10/2009 | Chinchoy |
| 7,610,092 B2 | 10/2009 | Cowan et al. |
| 7,610,099 B2 | 10/2009 | Almendinger et al. |
| 7,610,104 B2 | 10/2009 | Kaplan et al. |
| 7,616,991 B2 | 11/2009 | Mann et al. |
| 7,617,001 B2 | 11/2009 | Penner et al. |
| 7,617,007 B2 | 11/2009 | Williams et al. |
| 7,630,767 B1 | 12/2009 | Poore et al. |
| 7,634,313 B1 | 12/2009 | Kroll et al. |
| 7,637,867 B2 | 12/2009 | Zdeblick |
| 7,640,060 B2 | 12/2009 | Zdeblick |
| 7,647,109 B2 | 1/2010 | Hastings et al. |
| 7,650,186 B2 | 1/2010 | Hastings et al. |
| 7,657,311 B2 | 2/2010 | Bardy et al. |
| 7,668,596 B2 | 2/2010 | Von Arx et al. |
| 7,682,316 B2 | 3/2010 | Anderson et al. |
| 7,691,047 B2 | 4/2010 | Ferrari |
| 7,702,392 B2 | 4/2010 | Echt et al. |
| 7,713,194 B2 | 5/2010 | Zdeblick |
| 7,713,195 B2 | 5/2010 | Zdeblick |
| 7,729,783 B2 | 6/2010 | Michels et al. |
| 7,734,333 B2 | 6/2010 | Ghanem et al. |
| 7,734,343 B2 | 6/2010 | Ransbury et al. |
| 7,738,958 B2 | 6/2010 | Zdeblick et al. |
| 7,738,964 B2 | 6/2010 | Von Arx et al. |
| 7,742,812 B2 | 6/2010 | Ghanem et al. |
| 7,742,816 B2 | 6/2010 | Masoud et al. |
| 7,742,822 B2 | 6/2010 | Masoud et al. |
| 7,743,151 B2 | 6/2010 | Vallapureddy et al. |
| 7,747,335 B2 | 6/2010 | Williams |
| 7,751,881 B2 | 7/2010 | Cowan et al. |
| 7,758,521 B2 | 7/2010 | Morris et al. |
| 7,761,150 B2 | 7/2010 | Ghanem et al. |
| 7,761,164 B2 | 7/2010 | Verhoef et al. |
| 7,765,001 B2 | 7/2010 | Echt et al. |
| 7,769,452 B2 | 8/2010 | Ghanem et al. |
| 7,783,362 B2 | 8/2010 | Whitehurst et al. |
| 7,792,588 B2 | 9/2010 | Harding |
| 7,797,059 B1 | 9/2010 | Bornzin et al. |
| 7,801,596 B2 | 9/2010 | Fischell et al. |
| 7,809,438 B2 | 10/2010 | Echt et al. |
| 7,840,281 B2 | 11/2010 | Kveen et al. |
| 7,844,331 B2 | 11/2010 | Li et al. |
| 7,844,348 B2 | 11/2010 | Swoyer et al. |
| 7,846,088 B2 | 12/2010 | Ness |
| 7,848,815 B2 | 12/2010 | Brisken et al. |
| 7,848,823 B2 | 12/2010 | Drasler et al. |
| 7,860,455 B2 | 12/2010 | Fukumoto et al. |
| 7,871,433 B2 | 1/2011 | Lattouf |
| 7,877,136 B1 | 1/2011 | Moffitt et al. |
| 7,877,142 B2 | 1/2011 | Moaddeb et al. |
| 7,881,786 B2 | 2/2011 | Jackson |
| 7,881,798 B2 | 2/2011 | Miesel et al. |
| 7,881,810 B1 | 2/2011 | Chitre et al. |
| 7,890,173 B2 | 2/2011 | Brisken et al. |
| 7,890,181 B2 | 2/2011 | Denzene et al. |
| 7,890,192 B1 | 2/2011 | Kelsch et al. |
| 7,894,885 B2 | 2/2011 | Bartal et al. |
| 7,894,894 B2 | 2/2011 | Stadler et al. |
| 7,894,907 B2 | 2/2011 | Cowan et al. |
| 7,894,910 B2 | 2/2011 | Cowan et al. |
| 7,894,915 B1 | 2/2011 | Chitre et al. |
| 7,899,537 B1 | 3/2011 | Kroll et al. |
| 7,899,541 B2 | 3/2011 | Cowan et al. |
| 7,899,542 B2 | 3/2011 | Cowan et al. |
| 7,899,554 B2 | 3/2011 | Williams et al. |
| 7,901,360 B1 | 3/2011 | Yang et al. |
| 7,904,170 B2 | 3/2011 | Harding |
| 7,907,993 B2 | 3/2011 | Ghanem et al. |
| 7,920,928 B1 | 4/2011 | Yang et al. |
| 7,925,343 B1 | 4/2011 | Min et al. |
| 7,930,022 B2 | 4/2011 | Zhang et al. |
| 7,930,040 B1 | 4/2011 | Kelsch et al. |
| 7,937,135 B2 | 5/2011 | Ghanem et al. |
| 7,937,148 B2 | 5/2011 | Jacobson |
| 7,937,161 B2 | 5/2011 | Hastings et al. |
| 7,941,214 B2 | 5/2011 | Kleckner et al. |
| 7,945,333 B2 | 5/2011 | Jacobson |
| 7,946,997 B2 | 5/2011 | Hübinette |
| 7,949,404 B2 | 5/2011 | Hill |
| 7,949,405 B2 | 5/2011 | Feher |
| 7,953,486 B2 | 5/2011 | Daum et al. |
| 7,953,493 B2 | 5/2011 | Fowler et al. |
| 7,962,202 B2 | 6/2011 | Bhunia |
| 7,974,702 B1 | 7/2011 | Fain et al. |
| 7,979,136 B2 | 7/2011 | Young et al. |
| 7,983,753 B2 | 7/2011 | Severin |
| 7,991,467 B2 | 8/2011 | Markowitz et al. |
| 7,991,471 B2 | 8/2011 | Ghanem et al. |
| 7,996,087 B2 | 8/2011 | Cowan et al. |
| 8,000,791 B2 | 8/2011 | Sunagawa et al. |
| 8,000,807 B2 | 8/2011 | Morris et al. |
| 8,001,975 B2 | 8/2011 | DiSilvestro et al. |
| 8,002,700 B2 | 8/2011 | Ferek-Petric et al. |
| 8,010,209 B2 | 8/2011 | Jacobson |
| 8,019,419 B1 | 9/2011 | Panescu et al. |
| 8,019,434 B2 | 9/2011 | Quiles et al. |
| 8,027,727 B2 | 9/2011 | Freeberg |
| 8,027,729 B2 | 9/2011 | Sunagawa et al. |
| 8,032,219 B2 | 10/2011 | Neumann et al. |
| 8,036,743 B2 | 10/2011 | Savage et al. |
| 8,046,079 B2 | 10/2011 | Bange et al. |
| 8,046,080 B2 | 10/2011 | Von Arx et al. |
| 8,050,297 B2 | 11/2011 | Delmain et al. |
| 8,050,759 B2 | 11/2011 | Stegemann et al. |
| 8,050,774 B2 | 11/2011 | Kveen et al. |
| 8,055,345 B2 | 11/2011 | Li et al. |
| 8,055,350 B2 | 11/2011 | Roberts |
| 8,060,212 B1 | 11/2011 | Rios et al. |
| 8,065,018 B2 | 11/2011 | Haubrich et al. |

(56) References Cited

U.S. PATENT DOCUMENTS

| | | |
|---|---|---|
| 8,073,542 B2 | 12/2011 | Doerr |
| 8,078,278 B2 | 12/2011 | Penner |
| 8,078,283 B2 | 12/2011 | Cowan et al. |
| 8,095,123 B2 | 1/2012 | Gray |
| 8,102,789 B2 | 1/2012 | Rosar et al. |
| 8,103,359 B2 | 1/2012 | Reddy |
| 8,103,361 B2 | 1/2012 | Moser |
| 8,112,148 B2 | 2/2012 | Giftakis et al. |
| 8,114,021 B2 | 2/2012 | Robertson et al. |
| 8,121,680 B2 | 2/2012 | Falkenberg et al. |
| 8,123,684 B2 | 2/2012 | Zdeblick |
| 8,126,545 B2 | 2/2012 | Flach et al. |
| 8,131,334 B2 | 3/2012 | Lu et al. |
| 8,140,161 B2 | 3/2012 | Willerton et al. |
| 8,150,521 B2 | 4/2012 | Crowley et al. |
| 8,160,672 B2 | 4/2012 | Kim et al. |
| 8,160,702 B2 | 4/2012 | Mann et al. |
| 8,160,704 B2 | 4/2012 | Freeberg |
| 8,165,694 B2 | 4/2012 | Carbanaru et al. |
| 8,175,715 B1 | 5/2012 | Cox |
| 8,180,451 B2 | 5/2012 | Hickman et al. |
| 8,185,213 B2 | 5/2012 | Kveen et al. |
| 8,187,161 B2 | 5/2012 | Li et al. |
| 8,195,293 B2 | 6/2012 | Limousin et al. |
| 8,204,595 B2 | 6/2012 | Pianca et al. |
| 8,204,605 B2 | 6/2012 | Hastings et al. |
| 8,209,014 B2 | 6/2012 | Doerr |
| 8,214,043 B2 | 7/2012 | Matos |
| 8,224,244 B2 | 7/2012 | Kim et al. |
| 8,229,556 B2 | 7/2012 | Li |
| 8,233,985 B2 | 7/2012 | Bulkes et al. |
| 8,265,748 B2 | 9/2012 | Liu et al. |
| 8,265,757 B2 | 9/2012 | Mass et al. |
| 8,262,578 B1 | 10/2012 | Bharmi et al. |
| 8,280,521 B2 | 10/2012 | Haubrich et al. |
| 8,285,387 B2 | 10/2012 | Utsi et al. |
| 8,290,598 B2 | 10/2012 | Boon et al. |
| 8,290,600 B2 | 10/2012 | Hastings et al. |
| 8,295,939 B2 | 10/2012 | Jacobson |
| 8,301,254 B2 | 10/2012 | Mosesov et al. |
| 8,315,701 B2 | 11/2012 | Cowan et al. |
| 8,315,708 B2 | 11/2012 | Berthelsdorf et al. |
| 8,321,021 B2 | 11/2012 | Kisker et al. |
| 8,321,036 B2 | 11/2012 | Brockway et al. |
| 8,332,036 B2 | 12/2012 | Hastings et al. |
| 8,335,563 B2 | 12/2012 | Stessman |
| 8,335,568 B2 | 12/2012 | Heruth et al. |
| 8,340,750 B2 | 12/2012 | Prakash et al. |
| 8,340,780 B2 | 12/2012 | Hastings et al. |
| 8,352,025 B2 | 1/2013 | Jacobson |
| 8,352,028 B2 | 1/2013 | Wenger |
| 8,352,038 B2 | 1/2013 | Mao et al. |
| 8,359,098 B2 | 1/2013 | Lund et al. |
| 8,364,261 B2 | 1/2013 | Stubbs et al. |
| 8,364,276 B2 | 1/2013 | Willis |
| 8,369,959 B2 | 2/2013 | Meskens |
| 8,369,962 B2 | 2/2013 | Abrahamson |
| 8,380,320 B2 | 2/2013 | Spital |
| 8,386,051 B2 | 2/2013 | Rys |
| 8,391,981 B2 | 3/2013 | Mosesov |
| 8,391,990 B2 | 3/2013 | Smith et al. |
| 8,406,874 B2 | 3/2013 | Liu et al. |
| 8,406,879 B2 | 3/2013 | Shuros et al. |
| 8,406,886 B2 | 3/2013 | Gaunt et al. |
| 8,412,352 B2 | 4/2013 | Griswold et al. |
| 8,417,340 B2 | 4/2013 | Goossen |
| 8,417,341 B2 | 4/2013 | Freeberg |
| 8,423,149 B2 | 4/2013 | Hennig |
| 8,428,722 B2 | 4/2013 | Verhoef et al. |
| 8,433,402 B2 | 4/2013 | Ruben et al. |
| 8,433,409 B2 | 4/2013 | Johnson et al. |
| 8,433,420 B2 | 4/2013 | Bange et al. |
| 8,447,412 B2 | 5/2013 | Dal Molin et al. |
| 8,452,413 B2 | 5/2013 | Young et al. |
| 8,457,740 B2 | 6/2013 | Osche |
| 8,457,742 B2 | 6/2013 | Jacobson |
| 8,457,744 B2 | 6/2013 | Janzig et al. |
| 8,457,761 B2 | 6/2013 | Wariar |
| 8,478,407 B2 | 7/2013 | Demmer et al. |
| 8,478,408 B2 | 7/2013 | Hastings et al. |
| 8,478,431 B2 | 7/2013 | Griswold et al. |
| 8,494,632 B2 | 7/2013 | Sun et al. |
| 8,504,156 B2 | 8/2013 | Bonner et al. |
| 8,509,910 B2 | 8/2013 | Sowder et al. |
| 8,515,559 B2 | 8/2013 | Roberts et al. |
| 8,525,340 B2 | 9/2013 | Eckhardt et al. |
| 8,527,068 B2 | 9/2013 | Ostroff |
| 8,532,790 B2 | 9/2013 | Griswold |
| 8,538,526 B2 | 9/2013 | Stahmann et al. |
| 8,541,131 B2 | 9/2013 | Lund et al. |
| 8,543,205 B2 | 9/2013 | Ostroff |
| 8,547,248 B2 | 10/2013 | Zdeblick et al. |
| 8,548,605 B2 | 10/2013 | Ollivier |
| 8,554,333 B2 | 10/2013 | Wu et al. |
| 8,565,882 B2 | 10/2013 | Matos |
| 8,565,897 B2 | 10/2013 | Regnier et al. |
| 8,571,678 B2 | 10/2013 | Wang |
| 8,577,327 B2 | 11/2013 | Makdissi et al. |
| 8,588,926 B2 | 11/2013 | Moore et al. |
| 8,612,002 B2 | 12/2013 | Faltys et al. |
| 8,615,310 B2 | 12/2013 | Khairkhahan et al. |
| 8,626,280 B2 | 1/2014 | Allavatam et al. |
| 8,626,294 B2 | 1/2014 | Sheldon et al. |
| 8,634,908 B2 | 1/2014 | Cowan |
| 8,634,912 B2 | 1/2014 | Bornzin et al. |
| 8,634,919 B1 | 1/2014 | Hou et al. |
| 8,639,335 B2 | 1/2014 | Peichel et al. |
| 8,644,934 B2 | 2/2014 | Hastings et al. |
| 8,649,859 B2 | 2/2014 | Smith et al. |
| 8,670,842 B1 | 3/2014 | Bornzin et al. |
| 8,676,319 B2 | 3/2014 | Knoll |
| 8,676,335 B2 | 3/2014 | Katoozi et al. |
| 8,700,173 B2 | 4/2014 | Edlund |
| 8,700,181 B2 | 4/2014 | Bornzin et al. |
| 8,705,599 B2 | 4/2014 | dal Molin et al. |
| 8,718,766 B2 | 5/2014 | Wahlberg |
| 8,718,773 B2 | 5/2014 | Willis et al. |
| 8,725,260 B2 | 5/2014 | Shuros et al. |
| 8,738,133 B2 | 5/2014 | Shuros et al. |
| 8,738,147 B2 | 5/2014 | Hastings et al. |
| 8,744,555 B2 | 6/2014 | Allavatam et al. |
| 8,744,572 B1 | 6/2014 | Greenhut et al. |
| 8,747,314 B2 | 6/2014 | Stahmann et al. |
| 8,755,884 B2 | 6/2014 | Demmer et al. |
| 8,758,365 B2 | 6/2014 | Bonner et al. |
| 8,768,483 B2 | 7/2014 | Schmitt et al. |
| 8,774,572 B2 | 7/2014 | Hamamoto |
| 8,781,605 B2 | 7/2014 | Bornzin et al. |
| 8,788,035 B2 | 7/2014 | Jacobson |
| 8,788,053 B2 | 7/2014 | Jacobson |
| 8,798,740 B2 | 8/2014 | Samade et al. |
| 8,798,745 B2 | 8/2014 | Jacobson |
| 8,798,762 B2 | 8/2014 | Fain et al. |
| 8,798,770 B2 | 8/2014 | Reddy |
| 8,805,505 B1 | 8/2014 | Roberts |
| 8,805,528 B2 | 8/2014 | Corndorf |
| 8,812,109 B2 | 8/2014 | Blomqvist et al. |
| 8,818,504 B2 | 8/2014 | Bodner et al. |
| 8,827,913 B2 | 9/2014 | Havel et al. |
| 8,831,747 B1 | 9/2014 | Min et al. |
| 8,855,789 B2 | 10/2014 | Jacobson |
| 8,868,186 B2 | 10/2014 | Kroll |
| 8,886,339 B2 | 11/2014 | Faltys et al. |
| 8,903,473 B2 | 12/2014 | Rogers et al. |
| 8,903,500 B2 | 12/2014 | Smith et al. |
| 8,903,513 B2 | 12/2014 | Ollivier |
| 8,909,336 B2 | 12/2014 | Navarro-Paredes et al. |
| 8,914,131 B2 | 12/2014 | Bornzin et al. |
| 8,923,795 B2 | 12/2014 | Makdissi et al. |
| 8,923,963 B2 | 12/2014 | Bonner et al. |
| 8,938,300 B2 | 1/2015 | Rosero |
| 8,942,806 B2 | 1/2015 | Sheldon et al. |
| 8,958,892 B2 | 2/2015 | Khairkhahan et al. |
| 8,977,358 B2 | 3/2015 | Ewert et al. |

(56) References Cited

U.S. PATENT DOCUMENTS

| | | |
|---|---|---|
| 8,989,873 B2 | 3/2015 | Locsin |
| 8,996,109 B2 | 3/2015 | Karst et al. |
| 9,002,467 B2 | 4/2015 | Smith et al. |
| 9,008,776 B2 | 4/2015 | Cowan et al. |
| 9,008,777 B2 | 4/2015 | Dianaty et al. |
| 9,014,818 B2 | 4/2015 | Deterre et al. |
| 9,017,341 B2 | 4/2015 | Bornzin et al. |
| 9,020,611 B2 | 4/2015 | Khairkhahan et al. |
| 9,037,262 B2 | 5/2015 | Regnier et al. |
| 9,042,984 B2 | 5/2015 | Demmer et al. |
| 9,072,911 B2 | 7/2015 | Hastings et al. |
| 9,072,913 B2 | 7/2015 | Jacobson |
| 9,155,882 B2 | 10/2015 | Grubac et al. |
| 9,168,372 B2 | 10/2015 | Fain |
| 9,168,380 B1 | 10/2015 | Greenhut et al. |
| 9,168,383 B2 | 10/2015 | Jacobson et al. |
| 9,180,285 B2 | 11/2015 | Moore et al. |
| 9,192,774 B2 | 11/2015 | Jacobson |
| 9,205,225 B2 | 12/2015 | Khairkhahan et al. |
| 9,216,285 B1 | 12/2015 | Boling et al. |
| 9,216,293 B2 | 12/2015 | Berthiaume et al. |
| 9,216,298 B2 | 12/2015 | Jacobson |
| 9,227,077 B2 | 1/2016 | Jacobson |
| 9,238,145 B2 | 1/2016 | Wenzel et al. |
| 9,242,102 B2 | 1/2016 | Khairkhahan et al. |
| 9,242,113 B2 | 1/2016 | Smith et al. |
| 9,248,300 B2 | 2/2016 | Rys et al. |
| 9,265,436 B2 | 2/2016 | Min et al. |
| 9,265,962 B2 | 2/2016 | Dianaty et al. |
| 9,272,155 B2 | 3/2016 | Ostroff |
| 9,278,218 B2 | 3/2016 | Karst et al. |
| 9,278,229 B1 | 3/2016 | Reinke et al. |
| 9,283,381 B2 | 3/2016 | Grubac et al. |
| 9,283,382 B2 | 3/2016 | Berthiaume et al. |
| 9,289,612 B1 | 3/2016 | Sambelashvili et al. |
| 9,302,115 B2 | 4/2016 | Molin et al. |
| 9,333,364 B2 | 5/2016 | Echt et al. |
| 9,358,387 B2 | 6/2016 | Suwito et al. |
| 9,358,400 B2 | 6/2016 | Jacobson |
| 9,364,675 B2 | 6/2016 | Deterre et al. |
| 9,370,663 B2 | 6/2016 | Moulder |
| 9,375,580 B2 | 6/2016 | Bonner et al. |
| 9,375,581 B2 | 6/2016 | Baru et al. |
| 9,381,365 B2 | 7/2016 | Kibler et al. |
| 9,393,424 B2 | 7/2016 | Demmer et al. |
| 9,393,436 B2 | 7/2016 | Doerr |
| 9,399,139 B2 | 7/2016 | Demmer et al. |
| 9,399,140 B2 | 7/2016 | Cho et al. |
| 9,402,994 B2 | 8/2016 | Chow et al. |
| 9,409,033 B2 | 8/2016 | Jacobson |
| 9,427,594 B1 | 8/2016 | Bornzin et al. |
| 9,433,368 B2 | 9/2016 | Stahmann et al. |
| 9,433,780 B2 | 9/2016 | Régnier et al. |
| 9,492,668 B2 | 11/2016 | Sheldon et al. |
| 9,492,669 B2 | 11/2016 | Demmer et al. |
| 9,492,674 B2 | 11/2016 | Schmidt et al. |
| 9,492,677 B2 | 11/2016 | Greenhut et al. |
| 9,511,233 B2 | 12/2016 | Sambelashvili |
| 9,511,236 B2 | 12/2016 | Varady et al. |
| 9,511,237 B2 | 12/2016 | Deterre et al. |
| 2002/0032470 A1 | 3/2002 | Linberg |
| 2002/0035376 A1 | 3/2002 | Bardy et al. |
| 2002/0035377 A1 | 3/2002 | Bardy et al. |
| 2002/0035378 A1 | 3/2002 | Bardy et al. |
| 2002/0035380 A1 | 3/2002 | Rissmann et al. |
| 2002/0035381 A1 | 3/2002 | Bardy et al. |
| 2002/0042629 A1 | 4/2002 | Bardy et al. |
| 2002/0042630 A1 | 4/2002 | Bardy et al. |
| 2002/0042634 A1 | 4/2002 | Bardy et al. |
| 2002/0049475 A1 | 4/2002 | Bardy et al. |
| 2002/0052636 A1 | 5/2002 | Bardy et al. |
| 2002/0068958 A1 | 6/2002 | Bardy et al. |
| 2002/0072773 A1 | 6/2002 | Bardy et al. |
| 2002/0082665 A1 | 6/2002 | Haller et al. |
| 2002/0091414 A1 | 7/2002 | Bardy et al. |
| 2002/0095196 A1 | 7/2002 | Linberg |
| 2002/0099423 A1 | 7/2002 | Berg et al. |
| 2002/0103510 A1 | 8/2002 | Bardy et al. |
| 2002/0107545 A1 | 8/2002 | Rissmann et al. |
| 2002/0107546 A1 | 8/2002 | Ostroff et al. |
| 2002/0107547 A1 | 8/2002 | Erlinger et al. |
| 2002/0107548 A1 | 8/2002 | Bardy et al. |
| 2002/0107549 A1 | 8/2002 | Bardy et al. |
| 2002/0107559 A1 | 8/2002 | Sanders et al. |
| 2002/0120299 A1 | 8/2002 | Ostroff et al. |
| 2002/0173830 A1 | 11/2002 | Starkweather et al. |
| 2002/0193846 A1 | 12/2002 | Pool et al. |
| 2003/0009203 A1 | 1/2003 | Lebel et al. |
| 2003/0028082 A1 | 2/2003 | Thompson |
| 2003/0040779 A1 | 2/2003 | Engmark et al. |
| 2003/0041866 A1 | 3/2003 | Linberg et al. |
| 2003/0045805 A1 | 3/2003 | Sheldon et al. |
| 2003/0088278 A1 | 5/2003 | Bardy et al. |
| 2003/0097153 A1 | 5/2003 | Bardy et al. |
| 2003/0105497 A1 | 6/2003 | Zhu et al. |
| 2003/0114908 A1 | 6/2003 | Flach |
| 2003/0144701 A1 | 7/2003 | Mehra et al. |
| 2003/0187460 A1 | 10/2003 | Chin et al. |
| 2003/0187461 A1 | 10/2003 | Chin |
| 2004/0024435 A1 | 2/2004 | Leckrone et al. |
| 2004/0068302 A1 | 4/2004 | Rodgers et al. |
| 2004/0087938 A1 | 5/2004 | Leckrone et al. |
| 2004/0088035 A1 | 5/2004 | Guenst et al. |
| 2004/0102830 A1 | 5/2004 | Williams |
| 2004/0127959 A1 | 7/2004 | Amundson et al. |
| 2004/0133242 A1 | 7/2004 | Chapman et al. |
| 2004/0147969 A1 | 7/2004 | Mann et al. |
| 2004/0147973 A1 | 7/2004 | Hauser |
| 2004/0167558 A1 | 8/2004 | Igo et al. |
| 2004/0167587 A1 | 8/2004 | Thompson |
| 2004/0172071 A1 | 9/2004 | Bardy et al. |
| 2004/0172077 A1 | 9/2004 | Chinchoy |
| 2004/0172104 A1 | 9/2004 | Berg et al. |
| 2004/0176817 A1 | 9/2004 | Wahlstrand et al. |
| 2004/0176818 A1 | 9/2004 | Wahlstrand et al. |
| 2004/0176830 A1 | 9/2004 | Fang |
| 2004/0186529 A1 | 9/2004 | Bardy et al. |
| 2004/0204673 A1 | 10/2004 | Flaherty |
| 2004/0210292 A1 | 10/2004 | Bardy et al. |
| 2004/0210293 A1 | 10/2004 | Bardy et al. |
| 2004/0210294 A1 | 10/2004 | Bardy et al. |
| 2004/0215308 A1 | 10/2004 | Bardy et al. |
| 2004/0220624 A1 | 11/2004 | Ritscher et al. |
| 2004/0220626 A1 | 11/2004 | Wagner |
| 2004/0220639 A1 | 11/2004 | Mulligan et al. |
| 2004/0249431 A1 | 12/2004 | Ransbury et al. |
| 2004/0260348 A1 | 12/2004 | Bakken et al. |
| 2004/0267303 A1 | 12/2004 | Guenst |
| 2005/0061320 A1 | 3/2005 | Lee et al. |
| 2005/0070962 A1 | 3/2005 | Echt et al. |
| 2005/0102003 A1 | 5/2005 | Grabek et al. |
| 2005/0149138 A1 | 7/2005 | Min et al. |
| 2005/0165466 A1 | 7/2005 | Morris et al. |
| 2005/0182465 A1 | 8/2005 | Ness |
| 2005/0203410 A1 | 9/2005 | Jenkins |
| 2005/0283208 A1 | 12/2005 | Von Arx et al. |
| 2005/0288743 A1 | 12/2005 | Ahn et al. |
| 2006/0042830 A1 | 3/2006 | Maghribi et al. |
| 2006/0052829 A1 | 3/2006 | Sun et al. |
| 2006/0052830 A1 | 3/2006 | Spinelli et al. |
| 2006/0064135 A1 | 3/2006 | Brockway |
| 2006/0064149 A1 | 3/2006 | Belacazar et al. |
| 2006/0085039 A1 | 4/2006 | Hastings et al. |
| 2006/0085041 A1 | 4/2006 | Hastings et al. |
| 2006/0085042 A1 | 4/2006 | Hastings et al. |
| 2006/0095078 A1 | 5/2006 | Tronnes |
| 2006/0106442 A1 | 5/2006 | Richardson et al. |
| 2006/0116746 A1 | 6/2006 | Chin |
| 2006/0135999 A1 | 6/2006 | Bodner et al. |
| 2006/0136004 A1 | 6/2006 | Cowan et al. |
| 2006/0161061 A1 | 7/2006 | Echt et al. |
| 2006/0200002 A1 | 9/2006 | Guenst |
| 2006/0206151 A1 | 9/2006 | Lu |
| 2006/0212079 A1 | 9/2006 | Routh et al. |

(56) References Cited

U.S. PATENT DOCUMENTS

| | | |
|---|---|---|
| 2006/0241701 A1 | 10/2006 | Markowitz et al. |
| 2006/0241705 A1 | 10/2006 | Neumann et al. |
| 2006/0247672 A1 | 11/2006 | Vidlund et al. |
| 2006/0259088 A1 | 11/2006 | Pastore et al. |
| 2006/0265018 A1 | 11/2006 | Smith et al. |
| 2007/0004979 A1 | 1/2007 | Wojciechowicz et al. |
| 2007/0016098 A1 | 1/2007 | Kim et al. |
| 2007/0027508 A1 | 2/2007 | Cowan |
| 2007/0078490 A1 | 4/2007 | Cowan et al. |
| 2007/0088394 A1 | 4/2007 | Jacobson |
| 2007/0088396 A1 | 4/2007 | Jacobson |
| 2007/0088397 A1 | 4/2007 | Jacobson |
| 2007/0088398 A1 | 4/2007 | Jacobson |
| 2007/0088405 A1 | 4/2007 | Jacobson |
| 2007/0135882 A1 | 6/2007 | Drasler et al. |
| 2007/0135883 A1 | 6/2007 | Drasler et al. |
| 2007/0150037 A1 | 6/2007 | Hastings et al. |
| 2007/0150038 A1 | 6/2007 | Hastings et al. |
| 2007/0156190 A1 | 7/2007 | Cinbis |
| 2007/0219525 A1 | 9/2007 | Gelfand et al. |
| 2007/0219590 A1 | 9/2007 | Hastings et al. |
| 2007/0225545 A1 | 9/2007 | Ferrari |
| 2007/0233206 A1 | 10/2007 | Frikart et al. |
| 2007/0239244 A1 | 10/2007 | Morgan et al. |
| 2007/0255376 A1 | 11/2007 | Michels et al. |
| 2007/0276444 A1 | 11/2007 | Gelbart et al. |
| 2007/0293900 A1 | 12/2007 | Sheldon et al. |
| 2007/0293904 A1 | 12/2007 | Gelbart et al. |
| 2008/0004663 A1 | 1/2008 | Jorgenson |
| 2008/0021505 A1 | 1/2008 | Hastings et al. |
| 2008/0021519 A1 | 1/2008 | De Geest et al. |
| 2008/0021532 A1 | 1/2008 | Kveen et al. |
| 2008/0065183 A1 | 3/2008 | Whitehurst et al. |
| 2008/0065185 A1 | 3/2008 | Worley |
| 2008/0071318 A1 | 3/2008 | Brooke et al. |
| 2008/0109054 A1 | 5/2008 | Hastings et al. |
| 2008/0119911 A1 | 5/2008 | Rosero |
| 2008/0130670 A1 | 6/2008 | Kim et al. |
| 2008/0154139 A1 | 6/2008 | Shuros et al. |
| 2008/0154322 A1 | 6/2008 | Jackson et al. |
| 2008/0228234 A1 | 9/2008 | Stancer |
| 2008/0234771 A1 | 9/2008 | Chinchoy et al. |
| 2008/0243217 A1 | 10/2008 | Wildon |
| 2008/0269814 A1 | 10/2008 | Rosero |
| 2008/0269825 A1 | 10/2008 | Chinchoy et al. |
| 2008/0275518 A1 | 11/2008 | Ghanem et al. |
| 2008/0275519 A1 | 11/2008 | Ghanem et al. |
| 2008/0288039 A1 | 11/2008 | Reddy |
| 2008/0294208 A1 | 11/2008 | Willis et al. |
| 2008/0294210 A1 | 11/2008 | Rosero |
| 2008/0306359 A1 | 12/2008 | Zdeblick et al. |
| 2009/0018599 A1 | 1/2009 | Hastings et al. |
| 2009/0024180 A1 | 1/2009 | Kisker et al. |
| 2009/0036941 A1 | 2/2009 | Corbucci |
| 2009/0048646 A1 | 2/2009 | Katoozi et al. |
| 2009/0062895 A1 | 3/2009 | Stahmann et al. |
| 2009/0082827 A1 | 3/2009 | Kveen et al. |
| 2009/0082828 A1 | 3/2009 | Ostroff |
| 2009/0088813 A1 | 4/2009 | Brockway et al. |
| 2009/0131907 A1 | 5/2009 | Chin et al. |
| 2009/0135886 A1 | 5/2009 | Robertson et al. |
| 2009/0143835 A1 | 6/2009 | Pastore et al. |
| 2009/0171408 A1 | 7/2009 | Solem |
| 2009/0171414 A1 | 7/2009 | Kelly et al. |
| 2009/0204163 A1 | 8/2009 | Shuros et al. |
| 2009/0204170 A1 | 8/2009 | Hastings et al. |
| 2009/0210024 A1 | 8/2009 | M. |
| 2009/0216292 A1 | 8/2009 | Pless et al. |
| 2009/0234407 A1 | 9/2009 | Hastings et al. |
| 2009/0234411 A1 | 9/2009 | Sambelashvili et al. |
| 2009/0266573 A1 | 10/2009 | Engmark et al. |
| 2009/0275998 A1 | 11/2009 | Burnes et al. |
| 2009/0275999 A1 | 11/2009 | Burnes et al. |
| 2009/0299447 A1 | 12/2009 | Jensen et al. |
| 2010/0013668 A1 | 1/2010 | Kantervik |
| 2010/0016911 A1 | 1/2010 | Willis et al. |
| 2010/0023085 A1 | 1/2010 | Wu et al. |
| 2010/0030061 A1 | 2/2010 | Canfield et al. |
| 2010/0030327 A1 | 2/2010 | Chatel |
| 2010/0042108 A1 | 2/2010 | Hibino |
| 2010/0056871 A1 | 3/2010 | Govari et al. |
| 2010/0063375 A1 | 3/2010 | Kassab et al. |
| 2010/0063562 A1 | 3/2010 | Cowan et al. |
| 2010/0094367 A1 | 4/2010 | Sen |
| 2010/0109966 A1 | 5/2010 | Mateychuk |
| 2010/0114209 A1 | 5/2010 | Krause et al. |
| 2010/0114214 A1 | 5/2010 | Morelli et al. |
| 2010/0125281 A1 | 5/2010 | Jacobson et al. |
| 2010/0168761 A1 | 7/2010 | Kassab et al. |
| 2010/0168819 A1 | 7/2010 | Freeberg |
| 2010/0198288 A1 | 8/2010 | Ostroff |
| 2010/0198304 A1 | 8/2010 | Wang |
| 2010/0217367 A1 | 8/2010 | Belson |
| 2010/0228308 A1 | 9/2010 | Cowan et al. |
| 2010/0234906 A1 | 9/2010 | Koh |
| 2010/0234924 A1 | 9/2010 | Willis |
| 2010/0241185 A1 | 9/2010 | Mahapatra et al. |
| 2010/0249729 A1 | 9/2010 | Morris et al. |
| 2010/0286744 A1 | 11/2010 | Echt et al. |
| 2010/0312309 A1 | 12/2010 | Harding |
| 2011/0022113 A1 | 1/2011 | Zdeblick et al. |
| 2011/0071586 A1 | 3/2011 | Jacobson |
| 2011/0077708 A1 | 3/2011 | Ostroff |
| 2011/0112600 A1 | 5/2011 | Cowan et al. |
| 2011/0118588 A1 | 5/2011 | Komblau et al. |
| 2011/0118810 A1 | 5/2011 | Cowan et al. |
| 2011/0137187 A1 | 6/2011 | Yang et al. |
| 2011/0144720 A1 | 6/2011 | Cowan et al. |
| 2011/0152970 A1 | 6/2011 | Jollota et al. |
| 2011/0160558 A1 | 6/2011 | Rassatt et al. |
| 2011/0160565 A1 | 6/2011 | Stubbs et al. |
| 2011/0160801 A1 | 6/2011 | Markowitz et al. |
| 2011/0160806 A1 | 6/2011 | Lyden et al. |
| 2011/0166620 A1 | 7/2011 | Cowan et al. |
| 2011/0166621 A1 | 7/2011 | Cowan et al. |
| 2011/0184491 A1 | 7/2011 | Kivi |
| 2011/0190835 A1 | 8/2011 | Brockway et al. |
| 2011/0190849 A1* | 8/2011 | Faltys ............... A61N 1/36053 607/50 |
| 2011/0208260 A1 | 8/2011 | Jacobson |
| 2011/0218587 A1 | 9/2011 | Jacobson |
| 2011/0230734 A1 | 9/2011 | Fain et al. |
| 2011/0237967 A1 | 9/2011 | Moore et al. |
| 2011/0245890 A1 | 10/2011 | Brisben et al. |
| 2011/0251660 A1 | 10/2011 | Griswold |
| 2011/0251662 A1 | 10/2011 | Griswold et al. |
| 2011/0270099 A1 | 11/2011 | Ruben et al. |
| 2011/0270339 A1 | 11/2011 | Murray, III et al. |
| 2011/0270340 A1 | 11/2011 | Pellegrini et al. |
| 2011/0276102 A1 | 11/2011 | Cohen |
| 2011/0282423 A1 | 11/2011 | Jacobson |
| 2012/0004527 A1 | 1/2012 | Thompson et al. |
| 2012/0029323 A1 | 2/2012 | Zhao |
| 2012/0041508 A1 | 2/2012 | Rousso et al. |
| 2012/0059433 A1 | 3/2012 | Cowan et al. |
| 2012/0059436 A1 | 3/2012 | Fontaine et al. |
| 2012/0065500 A1 | 3/2012 | Rogers et al. |
| 2012/0078322 A1 | 3/2012 | Dal Molin et al. |
| 2012/0089198 A1 | 4/2012 | Ostroff |
| 2012/0093245 A1 | 4/2012 | Makdissi et al. |
| 2012/0095521 A1 | 4/2012 | Hintz |
| 2012/0095539 A1 | 4/2012 | Khairkhahan et al. |
| 2012/0101540 A1 | 4/2012 | O'Brien et al. |
| 2012/0101553 A1 | 4/2012 | Reddy |
| 2012/0109148 A1 | 5/2012 | Bonner et al. |
| 2012/0109149 A1 | 5/2012 | Bonner et al. |
| 2012/0109236 A1 | 5/2012 | Jacobson et al. |
| 2012/0109259 A1 | 5/2012 | Bond et al. |
| 2012/0116489 A1 | 5/2012 | Khairkhahan et al. |
| 2012/0150251 A1 | 6/2012 | Giftakis et al. |
| 2012/0158111 A1 | 6/2012 | Khairkhahan et al. |
| 2012/0165827 A1 | 6/2012 | Khairkhahan et al. |
| 2012/0172690 A1 | 7/2012 | Anderson et al. |
| 2012/0172891 A1 | 7/2012 | Lee |

(56) References Cited

U.S. PATENT DOCUMENTS

| | | |
|---|---|---|
| 2012/0172892 A1 | 7/2012 | Grubac et al. |
| 2012/0172942 A1 | 7/2012 | Berg |
| 2012/0197350 A1 | 8/2012 | Roberts et al. |
| 2012/0197373 A1 | 8/2012 | Khairkhahan et al. |
| 2012/0215285 A1 | 8/2012 | Tahmasian et al. |
| 2012/0232565 A1 | 9/2012 | Kveen et al. |
| 2012/0277600 A1 | 11/2012 | Greenhut |
| 2012/0277606 A1 | 11/2012 | Ellingson et al. |
| 2012/0283795 A1 | 11/2012 | Stancer et al. |
| 2012/0283807 A1 | 11/2012 | Deterre et al. |
| 2012/0290025 A1 | 11/2012 | Keimel |
| 2012/0296381 A1 | 11/2012 | Matos |
| 2012/0303082 A1 | 11/2012 | Dong et al. |
| 2012/0316613 A1 | 12/2012 | Keefe et al. |
| 2013/0012151 A1 | 1/2013 | Hankins |
| 2013/0023975 A1 | 1/2013 | Locsin |
| 2013/0035748 A1 | 2/2013 | Bonner et al. |
| 2013/0041422 A1 | 2/2013 | Jacobson |
| 2013/0053908 A1 | 2/2013 | Smith et al. |
| 2013/0053915 A1 | 2/2013 | Holmstrom et al. |
| 2013/0053921 A1 | 2/2013 | Bonner et al. |
| 2013/0060298 A1 | 3/2013 | Splett et al. |
| 2013/0066169 A1 | 3/2013 | Rys et al. |
| 2013/0066400 A1* | 3/2013 | Perryman .......... A61N 1/37229 607/59 |
| 2013/0072770 A1 | 3/2013 | Rao et al. |
| 2013/0079798 A1 | 3/2013 | Tran et al. |
| 2013/0079861 A1 | 3/2013 | Reinert et al. |
| 2013/0085350 A1 | 4/2013 | Schugt et al. |
| 2013/0085403 A1 | 4/2013 | Gunderson et al. |
| 2013/0085550 A1 | 4/2013 | Polefko et al. |
| 2013/0096649 A1 | 4/2013 | Martin et al. |
| 2013/0103047 A1 | 4/2013 | Steingisser et al. |
| 2013/0103109 A1 | 4/2013 | Jacobson |
| 2013/0110008 A1 | 5/2013 | Bourget et al. |
| 2013/0110127 A1 | 5/2013 | Bornzin et al. |
| 2013/0110192 A1 | 5/2013 | Tran et al. |
| 2013/0110219 A1 | 5/2013 | Bornzin et al. |
| 2013/0116529 A1 | 5/2013 | Min et al. |
| 2013/0116738 A1 | 5/2013 | Samade et al. |
| 2013/0116740 A1 | 5/2013 | Bornzin et al. |
| 2013/0116741 A1 | 5/2013 | Bornzin et al. |
| 2013/0123872 A1 | 5/2013 | Bornzin et al. |
| 2013/0123875 A1 | 5/2013 | Varady et al. |
| 2013/0131591 A1 | 5/2013 | Berthiaume et al. |
| 2013/0131693 A1 | 5/2013 | Berthiaume et al. |
| 2013/0138006 A1 | 5/2013 | Bornzin et al. |
| 2013/0150695 A1 | 6/2013 | Biela et al. |
| 2013/0150911 A1 | 6/2013 | Perschbacher et al. |
| 2013/0150912 A1 | 6/2013 | Perschbacher et al. |
| 2013/0184776 A1 | 7/2013 | Shuros et al. |
| 2013/0196703 A1 | 8/2013 | Masoud et al. |
| 2013/0197609 A1 | 8/2013 | Moore et al. |
| 2013/0231710 A1 | 9/2013 | Jacobson |
| 2013/0238072 A1 | 9/2013 | Deterre et al. |
| 2013/0238073 A1 | 9/2013 | Makdissi et al. |
| 2013/0253342 A1 | 9/2013 | Griswold et al. |
| 2013/0253343 A1 | 9/2013 | Waldhauser et al. |
| 2013/0253344 A1 | 9/2013 | Griswold et al. |
| 2013/0253345 A1 | 9/2013 | Griswold et al. |
| 2013/0253346 A1 | 9/2013 | Griswold et al. |
| 2013/0253347 A1 | 9/2013 | Griswold et al. |
| 2013/0261497 A1 | 10/2013 | Pertijs et al. |
| 2013/0265144 A1 | 10/2013 | Banna et al. |
| 2013/0268042 A1 | 10/2013 | Hastings et al. |
| 2013/0274828 A1 | 10/2013 | Willis |
| 2013/0274847 A1 | 10/2013 | Ostroff |
| 2013/0282070 A1 | 10/2013 | Cowan et al. |
| 2013/0282073 A1 | 10/2013 | Cowan et al. |
| 2013/0296727 A1 | 11/2013 | Sullivan et al. |
| 2013/0303872 A1 | 11/2013 | Taff et al. |
| 2013/0324825 A1 | 12/2013 | Ostroff et al. |
| 2013/0325081 A1 | 12/2013 | Karst et al. |
| 2013/0345770 A1 | 12/2013 | Dianaty et al. |
| 2014/0012344 A1 | 1/2014 | Hastings et al. |
| 2014/0018876 A1 | 1/2014 | Ostroff |
| 2014/0018877 A1 | 1/2014 | Demmer et al. |
| 2014/0031836 A1 | 1/2014 | Ollivier |
| 2014/0039570 A1 | 2/2014 | Carroll et al. |
| 2014/0039591 A1 | 2/2014 | Drasler et al. |
| 2014/0043146 A1 | 2/2014 | Makdissi et al. |
| 2014/0046395 A1 | 2/2014 | Regnier et al. |
| 2014/0046420 A1 | 2/2014 | Moore et al. |
| 2014/0058240 A1 | 2/2014 | Mothilal et al. |
| 2014/0058494 A1 | 2/2014 | Ostroff et al. |
| 2014/0074114 A1 | 3/2014 | Khairkhahan et al. |
| 2014/0074186 A1 | 3/2014 | Faltys et al. |
| 2014/0094891 A1 | 4/2014 | Pare et al. |
| 2014/0100627 A1 | 4/2014 | Min |
| 2014/0107723 A1 | 4/2014 | Hou et al. |
| 2014/0121719 A1 | 5/2014 | Bonner et al. |
| 2014/0121720 A1 | 5/2014 | Bonner et al. |
| 2014/0121722 A1 | 5/2014 | Sheldon et al. |
| 2014/0128932 A1 | 5/2014 | Ewert et al. |
| 2014/0128935 A1 | 5/2014 | Kumar et al. |
| 2014/0135865 A1 | 5/2014 | Hastings et al. |
| 2014/0142648 A1 | 5/2014 | Smith et al. |
| 2014/0148675 A1 | 5/2014 | Nordstrom et al. |
| 2014/0148815 A1 | 5/2014 | Wenzel et al. |
| 2014/0155950 A1 | 6/2014 | Hastings et al. |
| 2014/0169162 A1 | 6/2014 | Romano et al. |
| 2014/0172060 A1 | 6/2014 | Bornzin et al. |
| 2014/0180306 A1 | 6/2014 | Grubac et al. |
| 2014/0180366 A1 | 6/2014 | Edlund |
| 2014/0207149 A1 | 7/2014 | Hastings et al. |
| 2014/0207210 A1 | 7/2014 | Willis et al. |
| 2014/0214104 A1 | 7/2014 | Greenhurst et al. |
| 2014/0222098 A1 | 8/2014 | Baru et al. |
| 2014/0222109 A1 | 8/2014 | Moulder |
| 2014/0228913 A1 | 8/2014 | Molin et al. |
| 2014/0236172 A1 | 8/2014 | Hastings et al. |
| 2014/0243848 A1 | 8/2014 | Auricchio et al. |
| 2014/0255298 A1 | 9/2014 | Cole et al. |
| 2014/0257324 A1 | 9/2014 | Fain |
| 2014/0257422 A1 | 9/2014 | Herken |
| 2014/0257444 A1 | 9/2014 | Cole et al. |
| 2014/0276929 A1 | 9/2014 | Foster et al. |
| 2014/0303704 A1 | 10/2014 | Suwito et al. |
| 2014/0309706 A1 | 10/2014 | Jacobson |
| 2014/0379041 A1 | 12/2014 | Foster |
| 2015/0025612 A1 | 1/2015 | Haasl et al. |
| 2015/0039041 A1 | 2/2015 | Smith et al. |
| 2015/0051609 A1 | 2/2015 | Schmidt et al. |
| 2015/0051610 A1 | 2/2015 | Schmidt et al. |
| 2015/0051611 A1 | 2/2015 | Schmidt et al. |
| 2015/0051612 A1 | 2/2015 | Schmidt et al. |
| 2015/0051613 A1 | 2/2015 | Schmidt et al. |
| 2015/0051614 A1 | 2/2015 | Schmidt et al. |
| 2015/0051615 A1 | 2/2015 | Schmidt et al. |
| 2015/0051616 A1 | 2/2015 | Haasl et al. |
| 2015/0051682 A1 | 2/2015 | Schmidt et al. |
| 2015/0057520 A1 | 2/2015 | Foster et al. |
| 2015/0057558 A1 | 2/2015 | Stahmann et al. |
| 2015/0057721 A1 | 2/2015 | Stahmann et al. |
| 2015/0088155 A1 | 3/2015 | Stahmann et al. |
| 2015/0105836 A1 | 4/2015 | Bonner et al. |
| 2015/0157861 A1 | 6/2015 | Aghassian |
| 2015/0173655 A1 | 6/2015 | Demmer et al. |
| 2015/0190638 A1 | 7/2015 | Smith et al. |
| 2015/0196756 A1 | 7/2015 | Stahmann et al. |
| 2015/0196757 A1 | 7/2015 | Stahmann et al. |
| 2015/0196758 A1 | 7/2015 | Stahmann et al. |
| 2015/0196769 A1 | 7/2015 | Stahmann et al. |
| 2015/0217119 A1 | 8/2015 | Nikolski et al. |
| 2015/0221898 A1 | 8/2015 | Chi et al. |
| 2015/0224315 A1 | 8/2015 | Stahmann |
| 2015/0224320 A1 | 8/2015 | Stahmann |
| 2015/0258345 A1 | 9/2015 | Smith et al. |
| 2015/0290468 A1 | 10/2015 | Zhang |
| 2015/0297905 A1 | 10/2015 | Greenhut et al. |
| 2015/0297907 A1 | 10/2015 | Zhang |
| 2015/0305637 A1 | 10/2015 | Greenhut et al. |
| 2015/0305638 A1 | 10/2015 | Zhang |
| 2015/0305639 A1 | 10/2015 | Greenhut et al. |

(56) References Cited

U.S. PATENT DOCUMENTS

| | | |
|---|---|---|
| 2015/0305640 A1 | 10/2015 | Reinke et al. |
| 2015/0305641 A1 | 10/2015 | Stadler et al. |
| 2015/0305642 A1 | 10/2015 | Reinke et al. |
| 2015/0306374 A1 | 10/2015 | Seifert et al. |
| 2015/0306375 A1 | 10/2015 | Marshall et al. |
| 2015/0306406 A1 | 10/2015 | Crutchfield et al. |
| 2015/0306407 A1 | 10/2015 | Crutchfield et al. |
| 2015/0306408 A1 | 10/2015 | Greenhut et al. |
| 2015/0321016 A1 | 11/2015 | O'Brien et al. |
| 2015/0328459 A1 | 11/2015 | Chin et al. |
| 2016/0015322 A1 | 1/2016 | Anderson et al. |
| 2016/0023000 A1 | 1/2016 | Cho et al. |
| 2016/0030757 A1 | 2/2016 | Jacobson |
| 2016/0033177 A1 | 2/2016 | Barot et al. |
| 2016/0101291 A1 | 4/2016 | Jaax et al. |
| 2016/0121127 A1 | 5/2016 | Klimovitch et al. |
| 2016/0121128 A1 | 5/2016 | Fishler et al. |
| 2016/0121129 A1 | 5/2016 | Persson et al. |
| 2016/0213919 A1 | 7/2016 | Suwito et al. |
| 2016/0213937 A1 | 7/2016 | Reinke et al. |
| 2016/0213939 A1 | 7/2016 | Carney et al. |
| 2016/0228026 A1 | 8/2016 | Jackson |
| 2016/0317825 A1 | 11/2016 | Jacobson |
| 2017/0025888 A1 | 1/2017 | Cinbis et al. |

FOREIGN PATENT DOCUMENTS

| | | |
|---|---|---|
| AU | 2014203793 A1 | 7/2014 |
| CA | 1003904 A1 | 1/1977 |
| CN | 202933393 U | 5/2013 |
| EP | 0362611 A1 | 4/1990 |
| EP | 503823 A2 | 9/1992 |
| EP | 1702648 A2 | 9/2006 |
| EP | 1904166 B1 | 6/2011 |
| EP | 2433675 B1 | 1/2013 |
| EP | 2441491 B1 | 1/2013 |
| EP | 2452721 B1 | 11/2013 |
| EP | 1948296 B1 | 1/2014 |
| EP | 2662113 A3 | 1/2014 |
| EP | 2471452 B1 | 12/2014 |
| EP | 2760541 B1 | 5/2016 |
| EP | 2833966 B1 | 5/2016 |
| JP | 2000051373 A | 2/2000 |
| JP | 2002502640 A | 1/2002 |
| JP | 2004512105 A | 4/2004 |
| JP | 2005508208 A | 3/2005 |
| JP | 2005245215 A | 9/2005 |
| JP | 2008540040 A | 11/2008 |
| JP | 5199867 B2 | 2/2013 |
| WO | 9500202 A1 | 1/1995 |
| WO | 9636134 A1 | 11/1996 |
| WO | 9724981 A2 | 7/1997 |
| WO | 9826840 A1 | 6/1998 |
| WO | 9939767 A1 | 8/1999 |
| WO | 0234330 A2 | 1/2003 |
| WO | 02098282 A2 | 5/2003 |
| WO | 2005000206 A3 | 4/2005 |
| WO | 2005042089 A1 | 5/2005 |
| WO | 2006065394 A1 | 6/2006 |
| WO | 2006086435 A3 | 8/2006 |
| WO | 2006113659 A1 | 10/2006 |
| WO | 2006124833 A2 | 11/2006 |
| WO | 2006124833 A3 | 5/2007 |
| WO | 2007075974 A2 | 7/2007 |
| WO | 2009006531 A1 | 1/2009 |
| WO | 2012054102 A1 | 4/2012 |
| WO | 2013080038 A2 | 6/2013 |
| WO | 2013098644 A3 | 8/2013 |
| WO | 2013184787 A1 | 12/2013 |
| WO | 2014120769 A1 | 8/2014 |

OTHER PUBLICATIONS

International Search Report and Written Opinion for Application No. PCT/US2017/014139, 26 pages, dated Apr. 20, 2017.

Hachisuka et al., "Development and Performance Analysis of an Intra-Body Communication Device," The 12th International Conference on Solid State Sensors, Actuators and Microsystems, vol. 4A1.3, pp. 1722-1725, 2003.

Seyedi et al., "A Survey on Intrabody Communications for Body Area Network Application," IEEE Transactions on Biomedical Engineering,vol. 60(8): 2067-2079, 2013.

Wegmüller, "Intra-Body Communication for Biomedical Sensor Networks," Diss. ETH, No. 17323, 1-173, 2007.

Notification of Transmittal of the International Search Report and the Written Opinion of the International Searching Authority, or the Declaration, dated Jan. 29, 2016, 15 pages.

Spickler et al., "Totally Self-Contained Intracardiac Pacemaker," Journal of Electrocardiology, vol. 3(3&4): 324-331, 1970.

"Instructions for Use System 1, Leadless Cardiac Pacemaker (LCP) and Delivery Catheter," Nanostim Leadless Pacemakers, pp. 1-28, 2013.

* cited by examiner

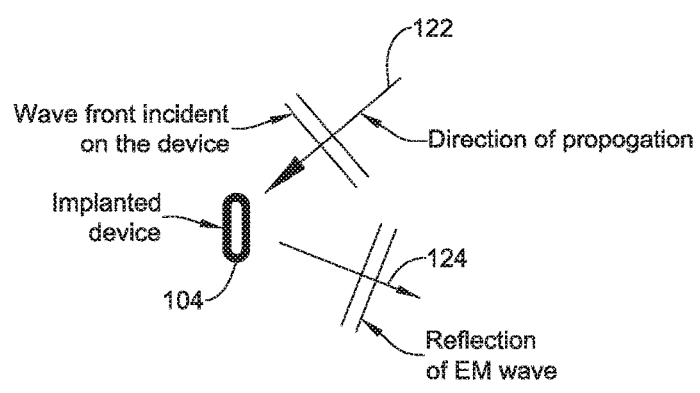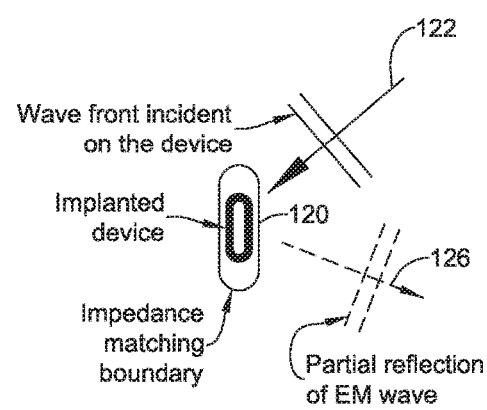
FIG. 12                                    FIG. 13

DEVICES AND METHODS FOR WIRELESSLY RECHARGING A RECHARGEABLE BATTERY OF AN IMPLANTABLE MEDICAL DEVICE

CROSS REFERENCE TO RELATED APPLICATIONS

This application claims the benefit of U.S. Provisional Patent Application Ser. No. 62/280,644 filed on Jan. 19, 2016, the disclosure of which is incorporated herein by reference.

TECHNICAL FIELD

The disclosure relates generally to implantable medical devices, and more particularly, to devices and methods for wirelessly recharging a rechargeable battery of an implanted medical device.

BACKGROUND

Cardiac pacemakers have been used to sense and pace heart rates for patients with a variety of incorrect heart rhythms, including but not limited to bradycardia, which is a slow heart rate. In some cases, a cardiac pacemaker may include a metal enclosure that contains control circuitry. Leads, which are electrically conductive, may be operatively coupled with the cardiac pacemaker and may extend into the circulatory system terminating in the heart. The leads often include pacing electrodes located at or near the distal end.

FIG. 1 shows a typical pacemaker system having a pacemaker can 10 and one or more leads, where only one lead 12 is shown in FIG. 1. Pacemaker can 10 is shown placed in a pocket in the upper chest area. The lead 12 is shown extending from the pacemaker can 10 and through the left subclavian vein, through the superior vena cava, and down into the patient's right ventricle, terminating in an electrode 14. In the example shown, the pacemaker can 10 is implanted external to the heart H while the lead 12 passes into the heart H, and places the electrode 14 at the ventricle wall of the heart H. In some cases, the lead 12 can be a potential weak link in the pacemaker system. Possible complications from the lead 12 may include displacement or misplacement of the lead 12, lead fracture or perforation, and pocket infections at or near the pacemaker can 10. In some cases, the lead 12 may impede certain surgical procedures by getting in the way.

Leadless pacemakers are in development, and enjoy the potential benefit of not including or using leads. As seen in FIG. 2, an example leadless pacemaker 16 is shown disposed within the patient's right ventricle. In some cases, the leadless pacemaker 16 may be self-contained, including a power supply such as a battery, control circuitry and one or more electrodes that may be disposed on an outer surface of the leadless pacemaker 16. The leadless pacemaker 16 is shown disposed entirely within the heart H, and more specifically in the right ventricle of the heart H. Because the battery life of the leadless pacemaker 16 often determines the useful life expectancy of the leadless pacemaker 16, the battery is often made to consume a relatively large fraction of the internal volume of the leadless pacemaker 16. There is a desire, however, to reduce the size of such leadless pacemakers, while at the same time increase their useful life expectancy.

SUMMARY

The disclosure is directed to implantable medical devices such as leadless cardiac pacemakers that can provide a longer lasting power source within a smaller device housing. In some cases, a leadless cardiac pacemaker may include a rechargeable battery and an antenna. The antenna may be sized to be carried by the leadless cardiac pacemaker, and may be configured to capture sufficient Radio Frequency (RF) energy transmitted to the leadless cardiac pacemaker by a transmitter located outside of the patient's body to recharge the rechargeable battery faster than the rechargeable battery is depleted by powering the leadless cardiac pacemaker. Accordingly, since the rechargeable battery does not need to initially store sufficient energy to power the leadless cardiac pacemaker over its entire expected life, the battery itself and thus the leadless cardiac pacemaker may be made smaller while still meeting device longevity expectations. Alternatively, or in addition, since implanted devices may be challenging to explant, prolonging the devices' longevity is desirable. In some cases, a rechargeable battery may allow the implanted device to last the patients entire life.

In a first example, a charging system for remotely charging a battery of an implantable medical device is disclosed. The example charging system may include a transmitter configured to transmit Electro-Magnetic (EM) energy from outside of a patient's body to inside of the patient's body. The charging system may further include an implantable medical device configured to be implanted inside of the patient's body. The implantable medical device may be powered at least in part by a rechargeable battery and may be configured to receive at least part of the EM energy transmitted by the transmitter and to use the received EM energy to charge the rechargeable battery of the implantable medical device.

In some cases, the implantable medical device of the first example may include an antenna that is tuned to receive at least part of the EM energy transmitted by the transmitter. Alternatively or additionally, the antenna may include a metamaterial-based biomimetic antenna. Alternatively or additionally, the antenna may include a Van Atta array having one or more zero-phase transmission lines, wherein at least one of the one or more zero-phase transmission lines includes a plurality of inter-digitated capacitors and a plurality of shunt inductive stubs.

Alternatively or additionally to the first example discussed above, the implantable medical device may further include circuitry to convert the received EM energy into energy that can be used to charge the rechargeable battery.

Alternatively or additionally to the first example, the EM energy includes RF energy, and the implantable medical device includes a leadless cardiac pacemaker.

Alternatively or additionally to the first example, the transmitter is configured to provide a substantially constant power density along a path through the patient's body to the implantable medical device.

Alternatively or additionally to the first example, the transmitter is configured to provide a conical shaped electromagnetic wave propagation path having a maximum width adjacent the transmitter and narrowing toward the implantable medical device.

Alternatively or additionally to the first example, the implantable medical device includes a housing having an EM impedance and an impedance boundary layer extending over at least part of the housing. The impedance boundary layer may have an EM impedance that is between the EM impedance of the housing and the EM impedance of the patient's body adjacent the implantable medical device.

Alternatively or additionally to the first example, the impedance boundary layer may include conducting particles.

Alternatively or additionally to the first example, the impedance boundary layer may include two or more layers each having a different permittivity and/or permeability.

Alternatively or additionally to the first example, the implantable medical device may be configured to be implanted such that the implantable medical device is fluidly coupled with flowing blood for thermal dissipation, such as inside a chamber of the heart or in a vein or artery.

In a second example, an implantable medical device sized to be implanted within a patient's heart is disclosed. The example implantable medical device may include a housing and circuitry disposed within the housing. Two or more electrodes may be operatively coupled to the circuitry are exposed external to the housing. A rechargeable battery may be disposed within the housing and may be configured to power the circuitry. A receiving antenna may be operatively coupled to the circuitry and may be configured to receive transmitted Electro-Magnetic (EM) energy through the patient's body. The circuitry may be configured to use the received EM energy to charge the rechargeable battery of the implantable medical device.

Alternatively or additionally to the second example, the receiving antenna may include a metamaterial-based biomimetic antenna.

Alternatively or additionally to the second example, the receiving antenna may include a Van Atta array with one or more zero-phase transmission lines, and at least one of the one or more zero-phase transmission lines may include a plurality of inter-digitated capacitors and a plurality of shunt inductive stubs.

Alternatively or additionally to the second example, the housing has an EM impedance and the patient's body has an EM impedance adjacent the implantable medical device, wherein the implantable medical device may further include an impedance boundary layer that has an EM impedance that is between the EM impedance of the housing and the EM impedance of the patient's body adjacent the implantable medical device.

In a third example, an antenna assembly is disclosed. The example antenna assembly may include an antenna sized to be carried by an implantable medical device that is itself sized to be implanted in a heart of a human patient and that includes a rechargeable battery for powering the implantable medical device. The antenna may be tuned to a wavelength band of Electro-Magnetic (EM) energy that can be transmitted through the human patient, and may be configured to receive sufficient EM energy from the wavelength band of Electro-Magnetic (EM) to recharge the rechargeable battery of the implantable medical device at a rate faster than the rechargeable battery is depleted by powering the implantable medical device when the wavelength band of Electro-Magnetic (EM) energy is transmitted at an intensity that does not cause heat damage to the human patient. The antenna assembly may include one or more antenna output terminals for delivering the received EM energy to the implantable medical device.

Alternatively or additionally to the third example, the antenna assembly may further includes one or more diodes that are operatively coupled to the antenna for rectifying the received EM energy.

Alternatively or additionally to the third example, the antenna may include a metamaterial-based biomimetic antenna.

Alternatively or additionally to the third example, the antenna may include a Van Atta array having one or more zero-phase transmission lines, and wherein at least one of the one or more zero-phase transmission lines includes a plurality of inter-digitated capacitors and a plurality of shunt inductive stubs disposed along an effective electrical length of the antenna.

The above summary of some embodiments is not intended to describe each disclosed embodiment or every implementation of the present disclosure. The Figures, and Detailed Description, which follow, more particularly exemplify some of these embodiments.

BRIEF DESCRIPTION OF THE FIGURES

The disclosure may be more completely understood in consideration of the following detailed description in connection with the accompanying drawings, in which:

FIG. 12 is a schematic diagram of a wave front incident on an illustrative implanted device;

FIG. 13 is a schematic diagram of a wave front incident on an implanted device that includes an impedance boundary layer;

Figure 1:
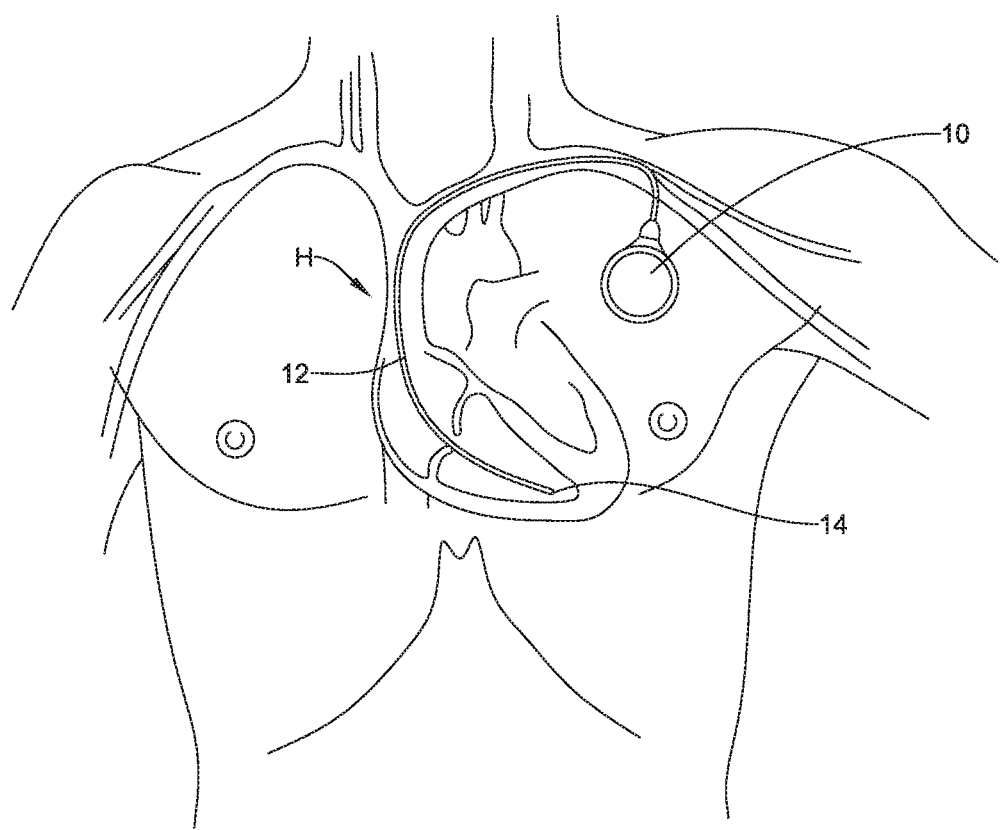
FIG. 1 is a schematic diagram of an implanted cardiac pacemaker.
Figure 2:
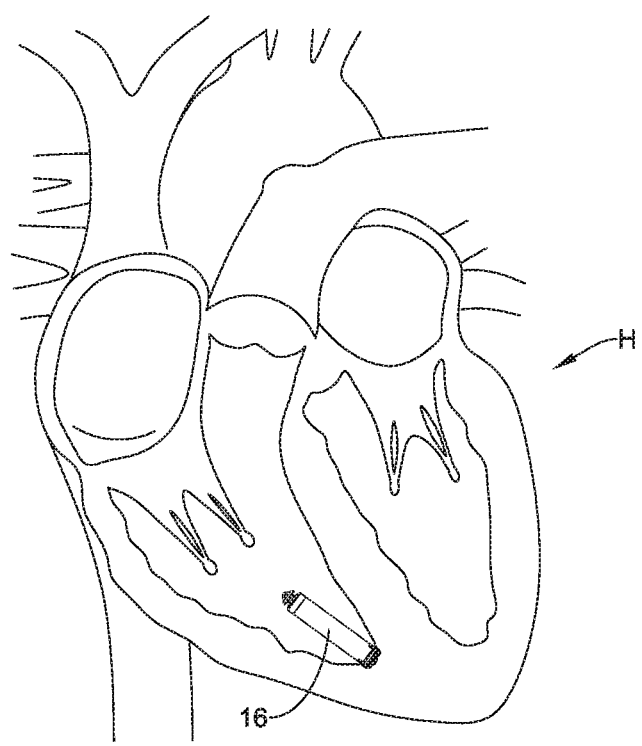
FIG. 2 is a schematic diagram of an implanted leadless cardiac pacemaker.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following description should be read with reference to the drawings in which similar structures in different drawings are numbered the same. The drawings, which are not necessarily to scale, depict illustrative embodiments and are not intended to limit the scope of the disclosure.

Figure 3:
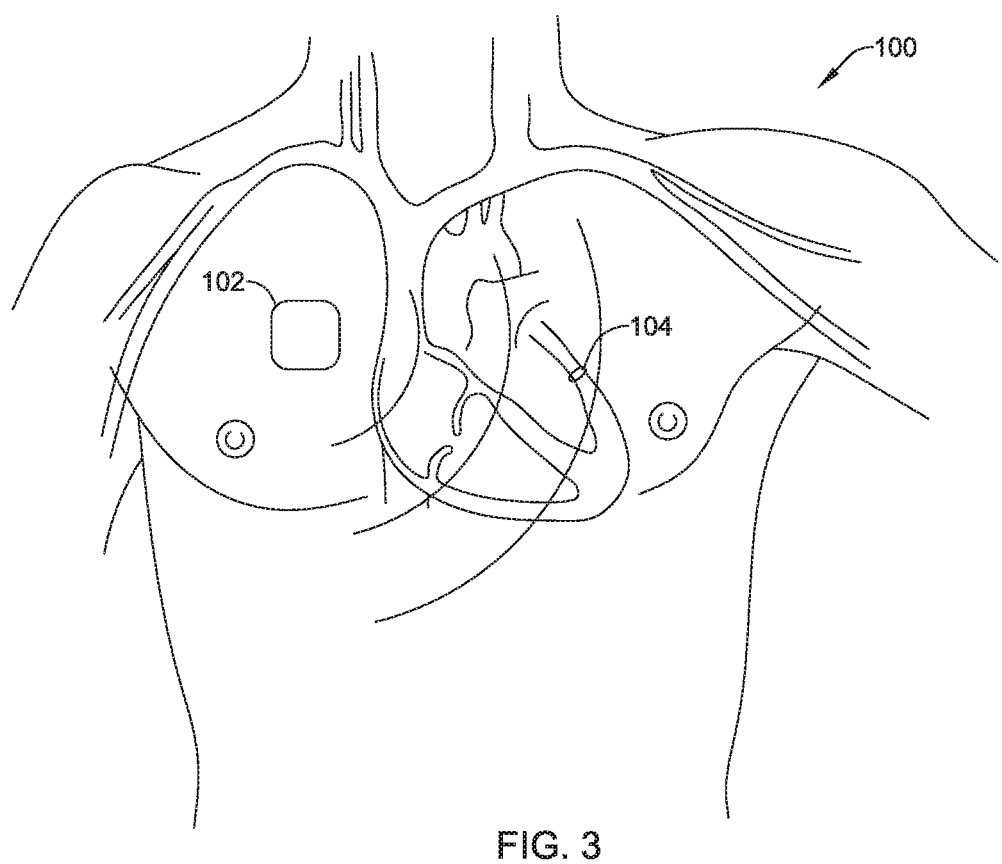
FIG. 3 is a schematic diagram of an illustrative remote wireless recharging system.

Turning to FIG. 3, which is a schematic diagram of an illustrative remote wireless recharging system 100. In its broadest terms, the illustrative remote wireless recharging system 100 includes a transmitter 102 and an implantable medical device 104. In some cases, the implantable medical device 104 may be configured to be implanted in or near the patient's heart H. In some instances, the implantable medical device 104 may be a leadless cardiac pacemaker (LCP). In some cases, the implantable medical device 104 may be configured to be implanted elsewhere within the patient's body and provide any desired functionality.

As illustrated in FIG. 3, the implantable medical device 104 has been implanted within the patient's heart H while the transmitter 102 remains outside of the patient's body. In some cases, the transmitter 102 may be disposed on the patient's skin or may otherwise be aimed towards the patient's chest. In some cases, the transmitter 102 may include a housing (not illustrated) that enables the transmitter 102 to be suspended from a lanyard that the patient can wear about their neck when it is time to recharge the implantable medical device 104. Overall, the transmitter may be configured to transmit electromagnetic (EM) energy from outside of the patient's body to inside the patient's body in order to transmit energy to the implantable medical device 104. In some cases, the EM energy may include RF energy. The implantable medical device 104 may then use captured energy to recharge a rechargeable battery disposed within the implantable medical device 104.

When considering the electromagnetic regions around a transmitting antenna, there are three categories; namely, (1) reactive near-field; (2) radiated near-field and (3) radiated far-field. "Inductive" charging systems operate in the reactive near-field region. In inductive power systems, power is typically transferred over short distances by magnetic fields using inductive coupling between coils of wire, or by electric fields using capacitive coupling between electrodes. In radiative power systems (e.g. radiated near-field and radiated far-field), power is typically transmitted by beams of electromagnetic (EM) energy. Radiative power systems can often transport energy for longer distances, but the ability of a receiving antenna to capture sufficient energy can be challenging, particular for applications where the size of the receiving antenna is limited.

In some cases, the transmitter 102 and implantable medical device 104 of the present disclosure may operate at or above about 400 MHz within the patient's body. When so provided, the system does not operate in the reactive near-field (as in inductive charging system), but rather operates in either the radiated near-field or radiated far-field regions (depending on the placement of the implanted device and band of usage). For example, when the EM energy is transmitted at 400 MHz, the system is in the radiated near-field region and at 2.45 GHz the system is in the radiated far-field region. In some cases, the present system may operate at a frequency that is between, for example, about 400 MHz and 3 GHz. In some cases, more than one frequency within this range may be used. When so provided, multiple implanted devices may be simultaneously or sequentially charged using both the radiated near-field and radiated far-field regions.

Figure 4:
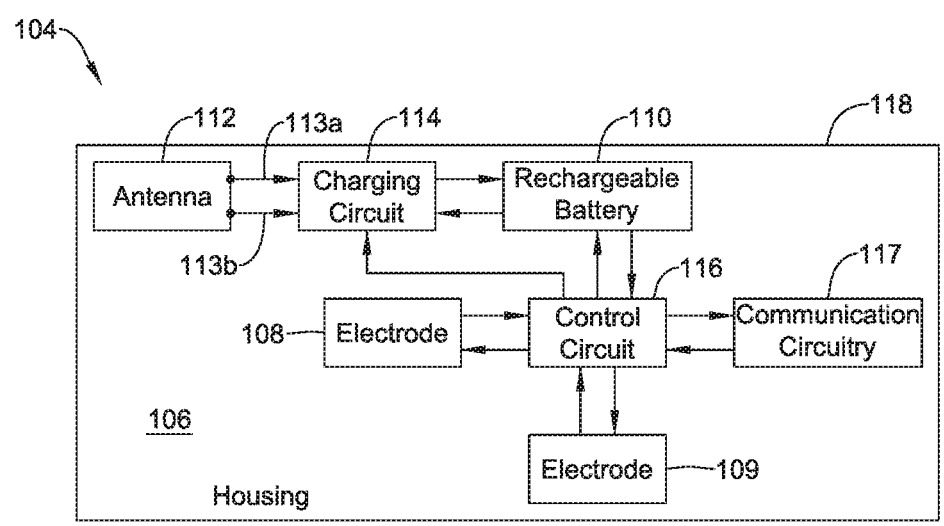
FIG. 4 is a schematic diagram of an illustrative implantable device usable within the illustrative remote charging system of FIG. 3.

FIG. 4 is a schematic diagram of the implantable medical device 104, illustrating some of the components that may be included. In some instances, the implantable medical device 104 may be sized to be implanted within a patient's heart H. The implantable medical device 104 may include a housing 106. A first electrode 108 and a second electrode 109 may be disposed relative to the housing 106. In some cases, the electrodes 108 and 109 may be exposed external to the housing 106, and in some cases, may be disposed on an outer surface of the housing 106. While two electrodes 108 and 109 are illustrated, in some cases there may be three or more distinct electrodes. The illustrative implantable medical device 104 also includes a rechargeable battery 110 that is disposed within the housing 106, and is used to power the operation of the implantable medical device 104. In some cases, the implantable medical device uses power from the rechargeable battery 110 to provide a voltage or current between to the electrodes 108 and 109 in order to pace the heart H, for example. In some cases, the electrodes 108 and 109 may be used as sense electrodes, and power from the rechargeable battery 110 may be used to process and/or communicate the signal(s) sensed by electrodes 108 and 109. In some cases, the implantable medical device 104 may provide a therapy such as a pacing therapy, a neurostimulation therapy, and/or any other suitable therapy. In some cases, the implantable medical device 104 may be merely a diagnostic device (e.g. no therapy provided), which collects diagnostic data and communicates the diagnostic data to a remote device. When so provided, the rechargeable battery 110 may provide energy to communicate the diagnostic data to a remote device.

The illustrative implantable medical device 104 also includes a receiving antenna 112, which may be disposed relative to the housing 106 and may be configured to receive transmitted EM energy from, for example, the transmitter 102 of FIG. 3. The antenna 112 may be an antenna assembly with one or more antenna output terminals 113a and 113b for delivering the received EM energy to the implantable medical device. In some cases, the antenna 112 may be sized to be carried by an implantable medical device 104 that is sized to be implanted in a heart of a human patient. The antenna 112 may be tuned to a wavelength band of Electro-Magnetic (EM) energy that can be transmitted through a human patient. The antenna may be configured to receive sufficient EM energy from the wavelength band of Electro-Magnetic (EM) to recharge the rechargeable battery 110 of the implantable medical device 104 at a rate faster than the rechargeable battery 110 is depleted by powering the implantable medical device 104, even when the wavelength band of Electro-Magnetic (EM) energy is transmitted at an intensity that is low enough to not cause heat damage to the human patient.

In the example shown, a power or charging circuit 114 may be configured to receive the transmitted EM energy received by the antenna 112 and convert at least some of the energy into a form (e.g. voltage and/or current) that can be used to recharge the rechargeable battery 110. In some cases, the antenna assembly 112 and/or the charging circuit 114 may include one or more diodes that are configured to half-wave or full-wave rectify the received signal to produce a power source for circuity (e.g. charging circuit 114, control circuit 116, and/or communication circuitry 117) of the implantable medical device 104. In the example shown, control circuit 116 may control the operation of the implantable medical device 104.

While not required, in some instances, the receiving antenna 112 may be a metamaterial-based biomimetic antenna. In some cases, the receiving antenna 112 may include a Van Atta array having at least one zero-phase transmission line. In some instances, the receiving antenna 112 may be a conformal antenna. In some cases, the receiving antenna 112 may include one or more antenna components that are printed on a substrate. In some cases, and as better shown in FIG. 7, the receiving antenna 112 may include a plurality of inter-digitated capacitors embedded within the receiving antenna 112. In some instances, and as also better shown in FIG. 7, the receiving antenna 112 may include shunt inductive stubs disposed along an effective electrical length of the receiving antenna 112.

For purposes of this disclosure, the phrase "metamaterial and biomimetic antenna" is herein defined as an antenna which uses metamaterials and nature inspired structures to increase the performance of miniaturized (electrically small) antenna systems. The term "metamaterials" is herein defined as materials engineered with microscopic structures to produce unusual physical properties. A "biomimetic antenna" is herein defined as an antenna that uses designs based on natural structures to improve the performance. By incorporating metamaterials and biomimetic sub-structures, these antennas can step up the receiving power of the antenna sometimes by increases the effective antenna aperture, while still being confined to a smaller form factor that is driven by the size of the implantable medical device for a given application.

Figure 5:
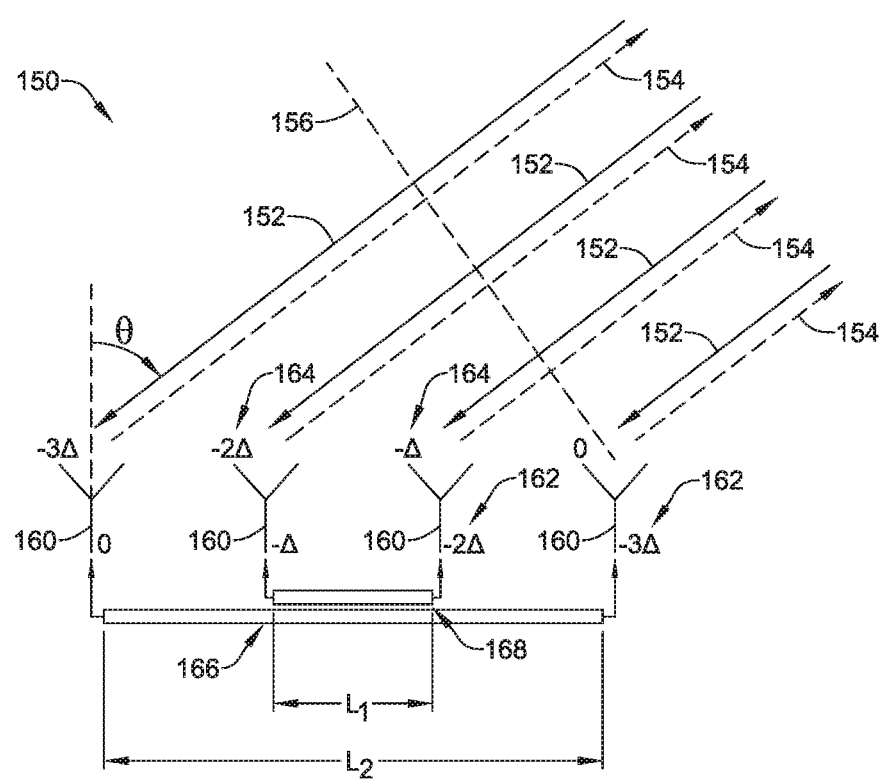
FIG. 5 is a schematic diagram of an illustrative antenna with a Van Atta array.

FIG. 5 is a schematic diagram of a metamaterial-based retrodirective (biomimetic) Van Atta array antenna configuration 150. The incident wave front is shown as a dashed line 156, running perpendicular to incident wave lines 152 and scattered waves 154. A Van Atta array 150 can receive electromagnetic waves from arbitrary directions and scatter the electromagnetic wave in the direction of the source automatically without the addition of additional circuitry (i.e. passive steering). This is achieved by connecting the antenna elements 160 shown in pairs symmetrically about the middle of the array. The inner antenna elements 160 are coupled by a first transmission line 168 to form the receive phase 164, and the outer antenna elements 160 are coupled by a second transmission line 166 to form the transmit phase 162. It will be appreciated that by choosing the lengths $L_1$ and $L_2$ of the connecting transmission lines 168 and 166 to be multiples of the guided wavelength of the source energy, the array is able to passively steer the beam in the direction of the source. This passive steering may be useful in supporting backscatter communication. However, when backscatter communication is not desired, the use of a Van Atta array antenna configuration 150 may be less compelling.

In some cases, diodes (not shown) may be inserted along each connecting transmission line 166, 168. When so provided, the array 150 may passively scan the region for EM energy and then use the connected diodes to full-wave rectify the signal to provide a DC power signal for powering digital and/or analog circuitry of an implantable medical device connected to the transmission lines 166, 168.

Figure 6:
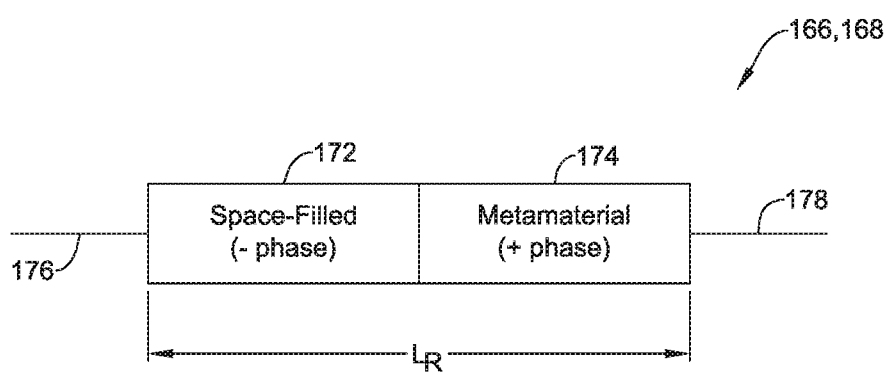
FIG. 6 is a schematic view of illustrative zero-phase transmission lines referenced in FIG. 5.

With reference to FIG. 6, connecting transmission lines 166, 168 essentially act as zero-phase transmission lines, meaning that the voltage and phase at both ends 176 and 178 of the transmission lines 166, 168 have both equal magnitude and phase. A transmission line is considered to be a zero-phase transmission line if the phase at both ends 176 and 178 is substantially the same (i.e. less than 30 degrees out of phase).

In some cases, a traditional transmission line has a negative phase constant introduced by the transmission line being a space-filling antenna construction. The illustrative array 150 of FIG. 6 uses a cascaded-hybrid metamaterial-based transmission line segment 174 and traditional transmission line segment 172 to significantly reduce the length of the transmission lines. A traditional space-filled transmission line has a negative phase constant, while a metamaterial-based transmission line has a positive phase constant. Cascading two such transmission lines 172 and 174 in the appropriate manner, such as shown in FIG. 6, results in a zero-phase transmission line (i.e., the phase introduced by the traditional transmission line is substantially removed by the metamaterial-based transmission line). This hybrid transmission line serves to reduce the effective transmission line length $L_R$, sometimes to about 0.25 to about 0.50 of the EM wavelength λ, less than 1 cm in length, and/or any other suitable length as desired). Therefore, by using metamaterial-based antenna elements in the cascaded transmission line 166, 168, an array for backscatter communications and power harvesting can be implemented on the embedded electrodes 18, 58, many times with a physical size of less than 1 cm, less than 0.5 cm, less than 0.1 cm, depending on the desired wavelength of the transmitted EM energy through the body.

Figure 7:
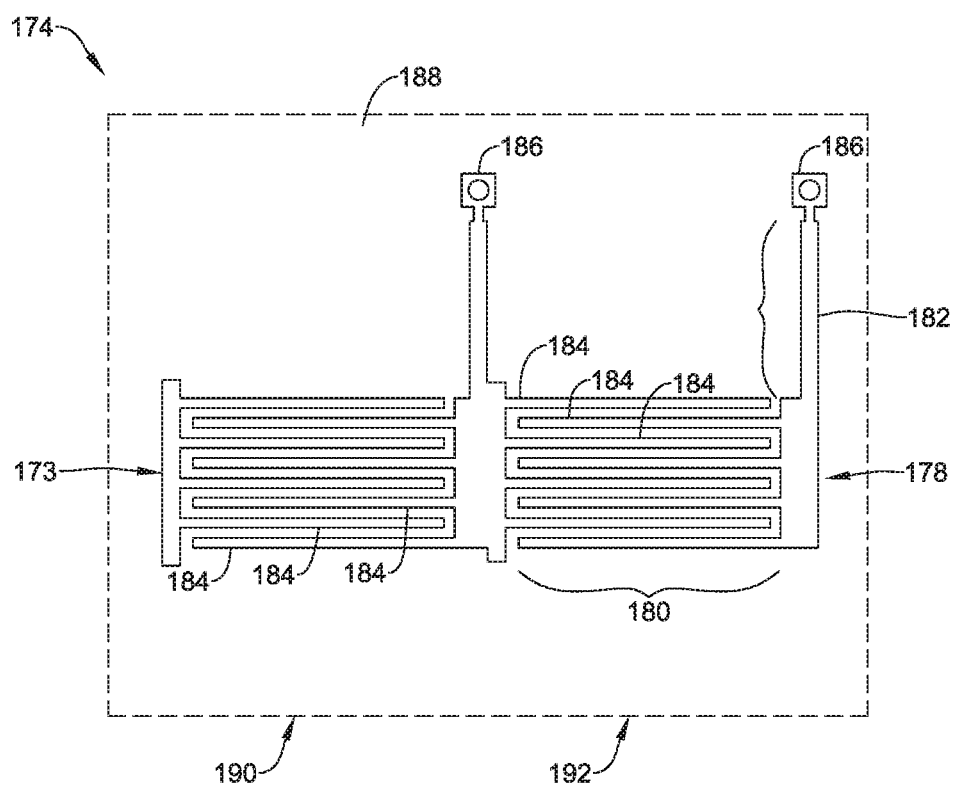
FIG. 7 is a schematic diagram of an illustrative metamaterial-based transmission line (MTL) element including two cascaded metamaterial circuits.
Figure 8:
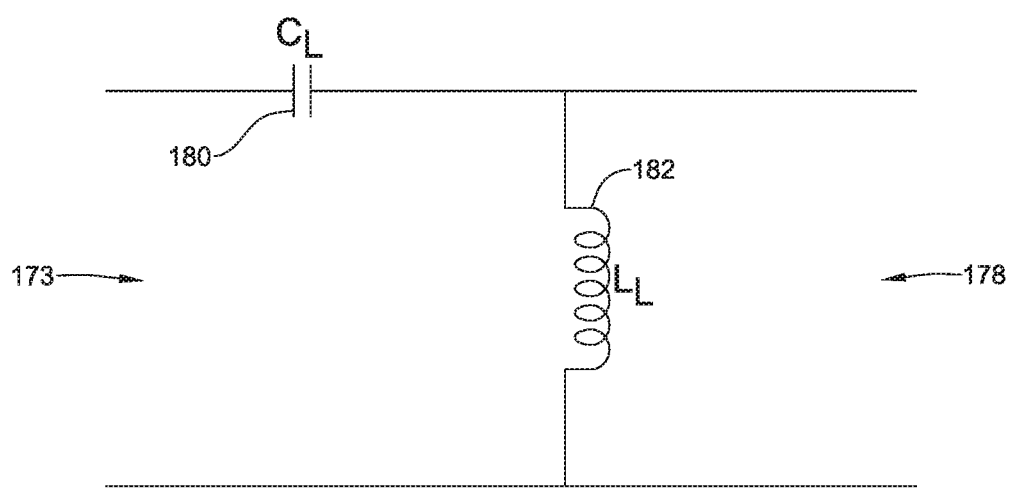
FIG. 8 shows an equivalent circuit of the two cascaded metamaterial circuits of FIG. 7.

FIG. 7 shows a schematic diagram of an exemplary metamaterial-based transmission line (MTL) element 174 including two cascaded metamaterial circuits 190 and 192. FIG. 8 shows an equivalent circuit of the two cascaded metamaterial circuits of FIG. 7. The illustrative MTL element 174 generally includes a series capacitance and a shunt inductance, which is intended to introduce a positive phase constant. As such, MTL element 174 includes one or more printed conductors 190, 192 on a conformal planar surface 188. While two circuits 190, 192 are shown in the embodiment of FIG. 7, it is appreciated that MTL element 174 may include one, two or more circuits. In some cases, the printed conductors 190, 192 are printed on a different layer than the printed reference plane 188. The wave from each antenna element in a Van Atta array is guided between the printed conductors 190, 192 via port 173 (coupled to the space-filled segment 172) and port 178. In the example shown, capacitance segment 180 includes interdigital capacitor fingers 184 that are used to introduce series capacitance. Each side of the interdigital capacitor has a printed conductor connected to a Via 186 that extends down to the reference plane 188 to introduce a shunt inductance 182. The equivalent circuit of the two cascaded metamaterial circuits 190 and 192 is shown in FIG. 8. In the example shown, a signal can be injected in port 173 and arrive at port 178, or a signal can be injected into port 178 and arrive at port 173 (a linear system).

Figure 9:
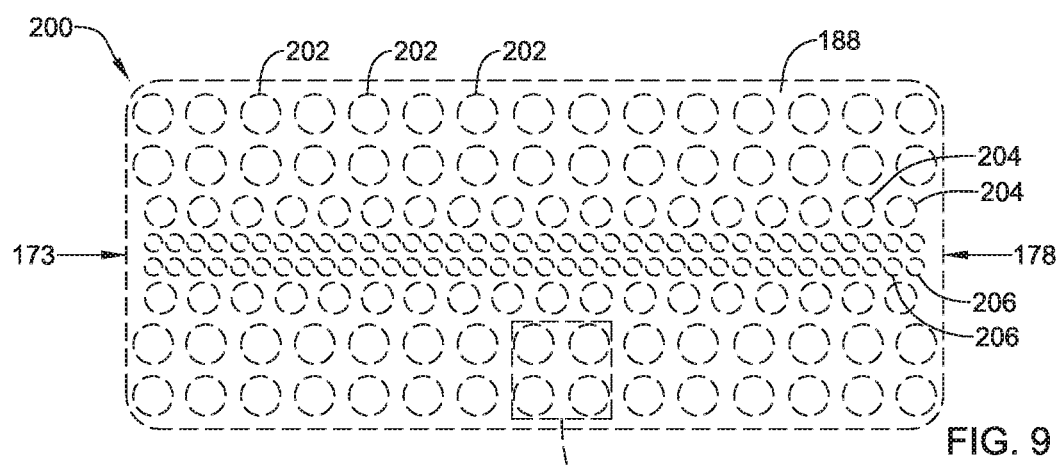
FIG. 9 is a planar MTL structure having a conformal topology.
Figure 10:
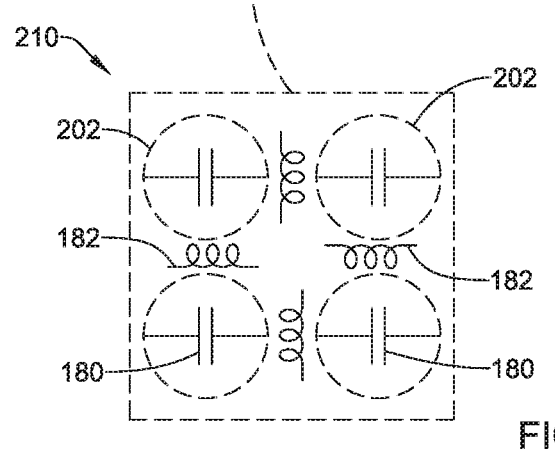
FIG. 10 is an equivalent circuit of a single unit cell of the planar MTL structure shown in FIG. 9.

FIG. 9 shows an alternate approach to using interdigitated capacitors and shunt inductors to realize a metamaterial transmission line. FIG. 9 shows a planar MTL structure 200 having a conformal topology. This topology has a single printed conducting plane 188 printed on a conformal surface with small apertures 202, 204 and 206 of the conductor removed. The wave from each antenna element in the Van Atta array is guided on this structure 200. By removing conducting material in a particular manner, a series capacitance and shunt inductance can be introduced for a guided wave between ports 173 and 178. The equivalent circuit 210 of a single unit cell of structure 200 is shown in FIG. 10. Each region with the removed conductor 188 (circle) can be modeled as a capacitor 180 in parallel with an inductor 182. By choosing the appropriate aperture size and spacing (e.g. large apertures 202, medium apertures 204, and small apertures 206), specific inductance and capacitance values can be introduced at various frequencies of interest. Therefore, if a wave is launched from port 173, it will immediately see conducting regions (e.g. large apertures 202) with a dominant capacitance (this introduces the required series capacitance for the positive phase advancement) and by using other regions with specific conducting regions removed near the end of the conducting plane 188, a shunt inductance (smaller apertures 206) can be introduced. Overall, the structure 200 will have the behavior of a metamaterial transmission line. While apertures 202, 204 and 206 are shown as circular openings in FIG. 10, it is appreciated that other shapes, e.g. rectangular hexagonal, etc., may be used.

Figure 11:
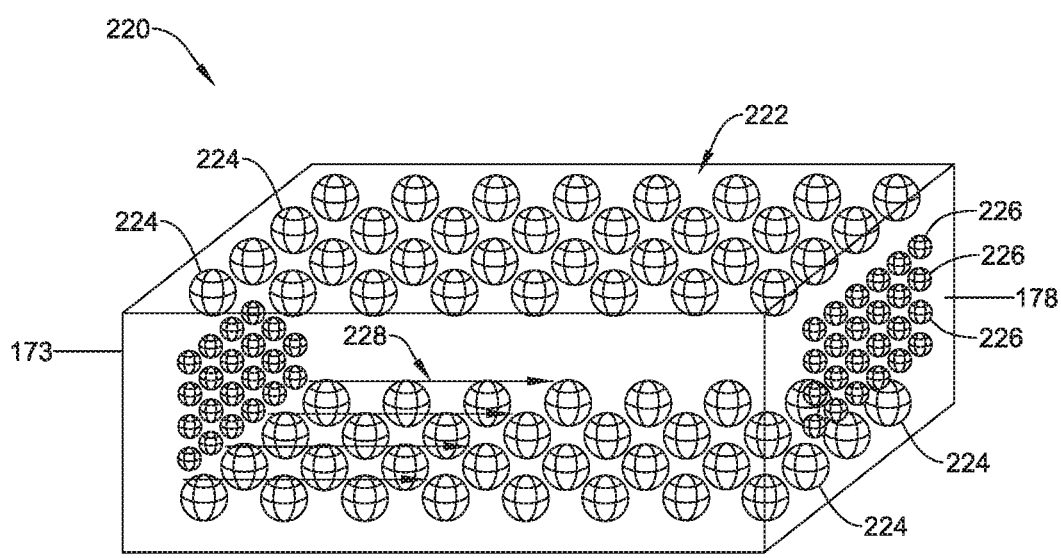
FIG. 11 is an MTL embodiment incorporating a 3D structure.

FIG. 11 shows a third illustrative MTL embodiment incorporating a 3D structure 220. This is a generalization of the 2D embodiment shown in FIGS. 9 and 10, except spheres 224 and 226 are used to control the series capacitance and inductance instead of circles in the plane of the conductor. In particular, the spherical material 224 and 226 may be embedded into a 3D host material 222. The spacing and spherical sizes are adapted to determine if the region is capacitively dominant or inductively dominant. This can then be used to synthesize a 3D metamaterial transmission line that shows phase advancement and zero phase properties.

Returning briefly to FIG. 4, in some cases, the housing 106 of the implantable medical device 104 may have an outer surface 118. In some cases, the outer surface 118 of the housing 106 may be configured to have an impedance that is similar to that of the tissue proximate an intended implantation site. As shown in FIGS. 12 and 13, the impedance of the outer surface 118 of the housing 106 may impact how effectively energy may be transmitted to the implantable medical device 104. An electromagnetic wave (EM) propagating in a medium has a wave impedance. In air this impedance is 377 Ohms for example. This wave impedance can be computed in a medium using the following equation:

$$Z_w = \sqrt{\frac{\mu}{\epsilon}} \text{ (Ohms)}$$

where $\mu$ is the total permeability of the medium the EM wave is propagating in and $\epsilon$ is the total permittivity of the medium the EM wave is propagating in. This expression holds for many different dielectrics and is a good estimate of the wave impedance within the body for the far-field. Next, when a wave is propagating in a medium and the constitutive parameters of either $\mu$ or $\epsilon$ change, the wave impedance changes. This results in a reflection of the EM wave off of that boundary. This can be seen in FIG. 12, in which an incident wave front 122 reflects off the implantable medical device 104 as a reflected EM wave 124. This can be detrimental to wireless recharging because there is energy in the reflected wave that does not propagate to the implantable medical device 104. This also occurs at the boundary between the tissue in which the implantable medical device 104 is embedded in and the materials forming the implantable medical device 104.

To help improve the recharging capabilities of this system, it may be useful to provide an impedance boundary layer to minimize this reflection. Such a boundary 120 is shown in FIG. 13 and can take on many different embodiments. As a result of including the boundary 120, it can be seen that the incident EM wave front 122 is only partially reflected as a partially reflected EM wave front 126.

In some cases, the housing 106 itself may be formed from a material(s) that have an EM impedance that substantially matches (e.g. within 10 percent) the EM impedance of the patient's body adjacent the implantable medical device 104. In other cases, an impedance boundary layer(s) 120 may be provided over at least part of the housing 106. The impedance boundary layer 120 may have an impedance value that is between the EM impedance of the housing 106 and an EM impedance of the patient's body adjacent the implantable medical device 104. There are several techniques for designing the impedance boundary layer(s) 120. For example, microscopic conducting particles with various shapes in a regular or irregular manner may be embedded within a thin layer on the surface of the implantable medical device 104. Alternatively, or in addition, the implantable medical device 104 may be coated with thin layers having different permittivities and/or permeabilities. As another example, conducting patterns may be printed on the surface of the housing 106 or on a thin insulating layer on the housing 106.

For example, by placing appropriate particles/elements in an impedance boundary layer(s), the wave impedance at the boundary can be tailored to be closer to the impedance of the tissue around the implantable medical device thereby reducing the amount of energy that is reflected by this boundary. In some cases, the wave impedance at the boundary may be tailored to be above, below or the same as the impedance of the tissue around the implantable medical device. In some cases, the wave impedance at the boundary is tailed to be:

$$Z_{boundary} = \sqrt{Z_{tissue} Z_{device}}$$

where $Z_{boundary}$ is the wave impedance at the boundary, $Z_{tissue}$ is the wave impedance in the tissue, and $Z_{device}$ is the wave impedance created by the material of the implantable medical device that is between the transmitter 102 and the antenna.

Figure 14:
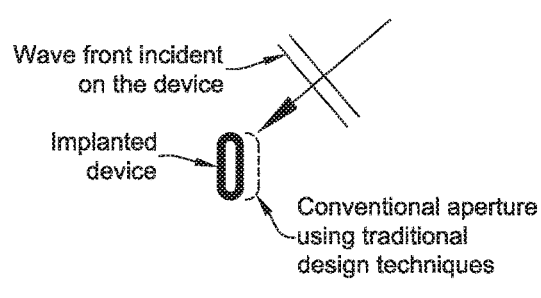
FIG. 14 is a schematic diagram of a wave front incident on an implanted device that includes an antenna with a smaller antenna aperture.

In some cases, if the power collection area of an antenna can be made larger than its actual physical size, then more power can be collected so that the transmitted power density in the surrounding tissue can be lowered. This can be accomplished by increasing the effective aperture Ae of the antenna, which is illustrated in FIG. 14. The effective aperture of an antenna can be computed using the following equation:

$$Ae=G\lambda^2/4\pi$$

where G (unit-less) is the gain of the antenna and λ (m) is the wavelength of the EM wave in the material around the antenna. Typically, the effective aperture is equal to or less than the physical size of the antenna, hence the units are in m². However, larger apertures can be achieved using antenna arrays or volumetric configurations. Also, while many antenna are designed to have a physical dimension that is comparable to the wavelength λ, which is defined as the electrical length of the antenna, we here disclose an antenna that is designed to have an electrical length that is larger than the wavelength of the EM wave λ. This can be accomplished by controlling the phase-constant over the structure of the antenna, which is denoted as β(rad/m) and related to λ by:

$$\lambda=2\pi/\beta.$$

Figure 15:
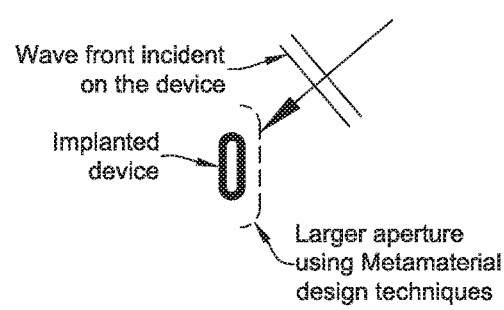
FIG. 15 is a schematic diagram of a wave front incident on an implanted device that includes an antenna with a larger antenna aperture.

As detailed above, the use of metamaterials and other techniques can reduce the phase-constant β of the antenna. This increases the value of λ, and by relation increases the value of Ae, the effective aperture of the antenna. An antenna having an increased effective aperture is shown in FIG. 15. Having an increased effective aperture increases the energy harvesting capabilities of the antenna, and thus the recharging capability of the implantable medical device 104. As detailed above, illustrative methods to control the value of β include: (1) embedding inter-digitated capacitors into the design of the antenna; and (2) using shunt inductive stubs in a periodic manner along the effective electrical length of the antenna.

For devices to be implanted within the body, the intensity of the energy transmitted by transmitter 102 is limited to prevent tissue damage in the patient (often through heating). Also, there is power loss as the EM wave passes through the body. As such, the amount of energy that can delivered to an implanted medical device is limited. To deliver sufficient energy to recharge a rechargeable battery of small implantable medical device in a reasonable amount of time (e.g. less than 1 day, less than 8 hours, less than 4 hours, less than 2 hours, less than 1 hour), the energy delivery must be relatively efficient.

Figure 16:
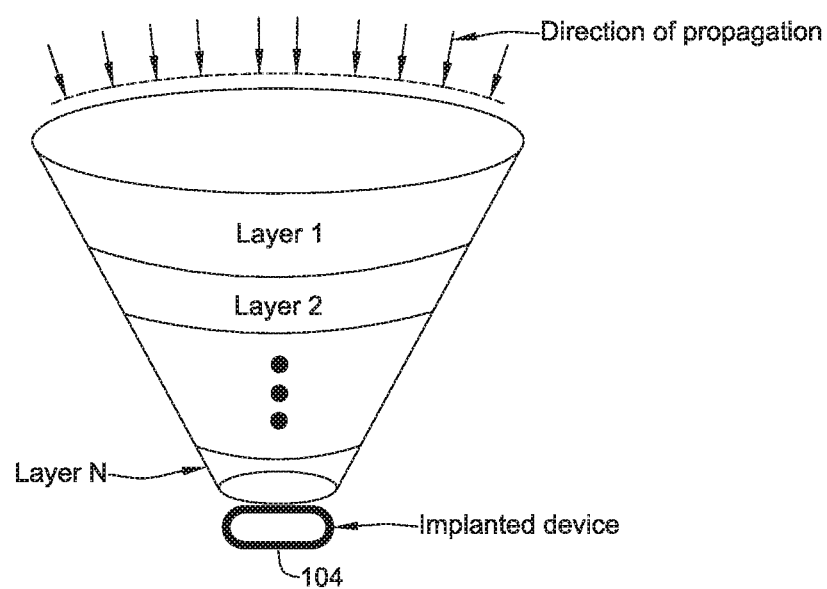
FIG. 16 is a schematic diagram of a conical electromagnetic wave propagation path.

To help improve the energy delivery efficiency, a conical wave propagation scheme as illustrated in FIG. 16 may be employed. Such a conical shape may be used to focus the transmitted energy on the implanted device and improve the recharging capabilities of the system. In some cases, the angle defining the cone may be chosen such that the power density at each layer from 1 to N along the length of the cone is substantially the same (within plus or minus 20 percent). Such an angle may be accomplished by active and/or passive beam steering by the transmitter 102. In some cases, the transmitter 102 may use a phased-array. Alternatively, or in addition, parasitic elements may be embedded in the body between the transmitter 102 on the surface and the implantable medical device 104 that help guide the transmitted energy to the implantable medical device 104.

Without such a system, as an EM wave propagates from a transmitter 102 and into the body, the energy radiates out in a radial manner spreading the energy density of the wave across an ever larger volume of tissue as the wave progresses into the body. By the time the wave arrives at the implantable medical device 104, the power density may be low, possibly too low for re-charging the rechargeable battery of the implantable medical device 104. The transmit power could be increased, but the energy density at the skin may exceed regulatory levels and possibly cause damage to the patient's tissue. When a conical propagation path is used, the power density along the path from the transmitter 102 to the implantable medical device 104 may be more controlled and focused, and in some cases, may be substantially constant (within plus or minus 20 percent) along the path.

Figure 17:
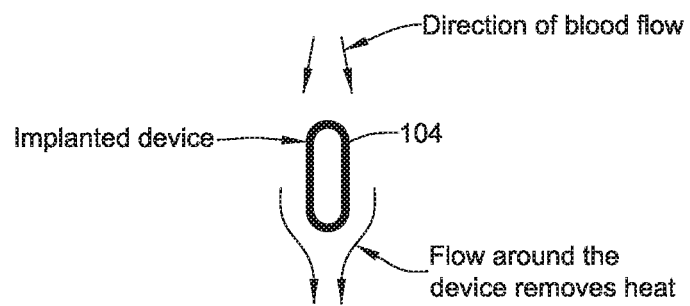
FIG. 17 is a schematic diagram showing heat removal around an implanted device by blood flow.

In some cases, as shown for example in FIG. 17, it may be useful to consider implanting the implantable medical device 104 at a location in the body in which the implantable medical device 104 is thermally coupled with a flowing fluid that can help dissipate heat that could otherwise build up as a result of EM energy impinging on the implantable medical device 104. For example, in some cases the implantable medical device 104 may be implanted in a location, such as within the heart H, wherein the implantable medical device 104 may be subjected to substantial blood flow.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. A charging system for remotely charging a rechargeable battery of an implantable medical device, comprising:
   a transmitter configured to transmit radiative Electro-Magnetic (EM) energy from outside of a patient's body to inside of the patient's body; and
   an implantable medical device configured to be implanted inside of the patient's body, wherein the implantable medical device includes a rechargeable battery, the implantable medical device being powered at least in part by the rechargeable battery, the implantable medical device configured to receive at least part of the radiative EM energy transmitted by the transmitter and to use the received radiative EM energy to charge the rechargeable battery of the implantable medical device.

2. The charging system of claim 1, wherein the implantable medical device comprises an antenna that is tuned to receive at least part of the radiative EM energy transmitted by the transmitter.

3. The charging system of claim 2, wherein the antenna comprises a metamaterial-based biomimetic antenna.

4. The charging system of claim 2, wherein the antenna comprises a Van Atta array comprising one or more zero-phase transmission lines, wherein at least one of the one or more zero-phase transmission lines comprises a plurality of inter-digitated capacitors and a plurality of shunt inductive stubs.

5. The charging system of claim 1, wherein the implantable medical device further comprises circuitry to convert the received radiative EM energy into energy that can be used to charge the rechargeable battery.

6. The charging system of claim 1, wherein the radiative EM energy comprises RF energy, and the implantable medical device comprises a leadless cardiac pacemaker.

7. The charging system of claim 1, wherein the transmitter is configured to provide a substantially constant power density along a path through the patient's body to the implantable medical device.

8. The charging system of claim 1, wherein the transmitter is configured to provide a conical shaped electromagnetic wave propagation path having a maximum width adjacent the transmitter and narrowing toward the implantable medical device.

9. The charging system of claim 1, wherein the implantable medical device comprises:
 a housing having an EM impedance; and
 an impedance boundary layer extending over at least part of the housing, the impedance boundary layer comprising an EM impedance between the EM impedance of the housing and the EM impedance of the patient's body adjacent the implantable medical device.

10. The charging system of claim 9, wherein the impedance boundary layer comprises conducting particles.

11. The charging system of claim 9, wherein the impedance boundary layer comprises two or more layers each having a different permittivity and/or permeability.

12. The charging system of claim 1, wherein the implantable medical device is configured to be implanted such that the implantable medical device is fluidly coupled with flowing blood for thermal dissipation.

13. An implantable medical device sized to be implanted within a patient's heart, the implantable medical device comprising:
 a housing;
 circuitry disposed within the housing;
 two or more electrodes exposed external to the housing, the two or more electrodes operatively coupled to the circuitry;
 a rechargeable battery disposed within the housing and configured to power the circuitry;
 a receiving antenna operatively coupled to the circuitry and configured to receive transmitted radiative Electro-Magnetic (EM) energy through the patient's body; and
 the circuitry configured to use the received radiative EM energy to charge the rechargeable battery of the implantable medical device.

14. The implantable medical device of claim 13, wherein the receiving antenna comprises a metamaterial-based biomimetic antenna.

15. The implantable medical device of claim 13, wherein the receiving antenna comprises a Van Atta array with one or more zero-phase transmission lines, and wherein at least one of the one or more zero-phase transmission lines comprises a plurality of inter-digitated capacitors and a plurality of shunt inductive stubs.

16. The implantable medical device of claim 13, wherein the housing has an EM impedance and the patient's body has an EM impedance adjacent the implantable medical device, wherein the implantable medical device further comprises an impedance boundary layer that has an EM impedance between the EM impedance of the housing and the EM impedance of the patient's body adjacent the implantable medical device.

17. An antenna assembly, comprising:
 an antenna sized to be carried by an implantable medical device, wherein the implantable medical device is sized to be implanted in a heart of a human patient and includes a rechargeable battery for powering the implantable medical device;
 the antenna tuned to a wavelength band of radiative Electro-Magnetic (EM) energy that can be transmitted through the human patient;
 the antenna is configured to receive sufficient radiative EM energy from the wavelength band of radiative Electro-Magnetic (EM) to recharge the rechargeable battery of the implantable medical device at a rate faster than the rechargeable battery is depleted by powering the implantable medical device when the wavelength band of radiative Electro-Magnetic (EM) energy is transmitted at an intensity that is low enough to not cause heat damage to the human patient; and
 one or more antenna output terminals for delivering the received radiative EM energy to the implantable medical device.

18. The antenna assembly of claim 17, further comprising one or more diodes operatively coupled to the antenna for rectifying the received radiative EM energy.

19. The antenna assembly of claim 17, wherein the antenna comprises a metamaterial-based biomimetic antenna.

20. The antenna assembly of claim 17, wherein the antenna comprises a Van Atta array comprising one or more zero-phase transmission lines, and wherein at least one of the one or more zero-phase transmission lines comprises a plurality of inter-digitated capacitors and a plurality of shunt inductive stubs disposed along an effective electrical length of the antenna.

* * * * *